United States Patent
Kaiser et al.

(10) Patent No.: US 8,755,881 B2
(45) Date of Patent: Jun. 17, 2014

(54) PACING THERAPY ADJUSTMENT BASED ON VENTRICULO-ATRIAL DELAY

(75) Inventors: Daniel R. Kaiser, Plymouth, MN (US); Nicholas D. Skadsberg, Blaine, MN (US); Steven R. Hornberger, Maple Grove, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1459 days.

(21) Appl. No.: 12/363,439

(22) Filed: Jan. 30, 2009

(65) Prior Publication Data

US 2010/0198293 A1  Aug. 5, 2010

(51) Int. Cl.
*A61N 1/365* (2006.01)
*A61N 1/368* (2006.01)

(52) U.S. Cl.
CPC ....................................... *A61N 1/368* (2013.01)
USPC .............................................................. 607/9

(58) Field of Classification Search
USPC ......................................... 607/4, 5, 9, 14, 25
See application file for complete search history.

(56) References Cited

U.S. PATENT DOCUMENTS

| | | | |
|---|---|---|---|
| 4,374,382 A | 2/1983 | Markowitz | |
| 4,378,020 A | 3/1983 | Nappholz et al. | |
| 5,117,824 A | 6/1992 | Keimel et al. | |
| 5,247,929 A | 9/1993 | Stoop et al. | |
| 5,545,186 A | 8/1996 | Olson et al. | |
| 5,755,736 A | 5/1998 | Gillberg et al. | |
| 7,130,683 B2 * | 10/2006 | Casavant et al. | 607/9 |
| 7,181,284 B2 | 2/2007 | Burnes et al. | |
| 2003/0083700 A1 | 5/2003 | Hill | |
| 2005/0137634 A1 | 6/2005 | Hall et al. | |
| 2005/0154421 A1 | 7/2005 | Ousdigian | |
| 2005/0209648 A1 | 9/2005 | Burnes et al. | |
| 2007/0191891 A1 | 8/2007 | Burnes et al. | |
| 2007/0191892 A1 | 8/2007 | Mullen et al. | |
| 2008/0269823 A1 | 10/2008 | Burnes et al. | |

OTHER PUBLICATIONS

Lee et al., "Avoidance of Right Ventricular Pacing in Cardiac Resynchronization Therapy Improves Right Ventricular Hemodynamics in Heart Failure Patients", Journal of Cardiovascular Electrophysiology, vol. 18, No. 8, pp. 1-8, Aug. 2007.

Vollmann, Dirk et al., "Biventricular Pacing Improves the Blunted Force-Frequency Relation Present During Univentricular Pacing in Patients With Heart Failure and Conduction Delay," Journal of the American Heart Association, Circulation 2006: 113; 953-959 (8 pgs.).

(Continued)

*Primary Examiner* — Christopher D Koharski
*Assistant Examiner* — Jeremiah Kimball
(74) *Attorney, Agent, or Firm* — Reed A. Duthler

(57) ABSTRACT

Techniques for adjusting pacing therapy based on ventriculo-atrial delay are described herein. These techniques may be used to control ventricular filling times during the delivery of pacing therapy. In some examples, a device or system delivers pre-excitation fusion pacing therapy to a ventricular chamber, determines a ventriculo-atrial delay interval for the ventricular chamber for at least one cardiac cycle, and adjusts the pacing therapy delivered by the implantable medical device to compensate for decreased ventricular filling time when the ventriculo-atrial delay interval is less than a threshold. In some examples, the device or system may adjust the pacing therapy by decreasing a pacing rate of the implantable medical device, increasing a pre-excitation interval for pacing of the ventricular chamber, and/or switching from a fusion pacing mode to a biventricular pacing mode.

30 Claims, 11 Drawing Sheets

(56) References Cited

OTHER PUBLICATIONS

Burkhoff, Daniel et al., "Influence of pacing site on canine left ventricular contraction," The American Physiological Society, Pacing Site and Ventricular Performance, pp. H429-H435 (8 pgs.).

Erenberg, Francine G. et al., "Systolic and Diastolic Properties of Univentricular Hearts in Children: Insights from Physiologic Indices That Reflect Calcium Cycling," Pediatric Research, vol. 54, No. 6, 2003 (7 pgs.).

(PCT/US2010/020850) PCT Notification of Transmittal of the International Search Report and the Written Opinion of the International Searching Authority.

* cited by examiner

PACING THERAPY ADJUSTMENT BASED ON VENTRICULO-ATRIAL DELAY

TECHNICAL FIELD

The disclosure relates to implantable medical devices, and, more particularly, to implantable medical devices that deliver electrical stimulation therapy to a patient.

BACKGROUND

Some types of implantable medical devices, such as cardiac pacemakers or implantable cardioverter defibrillators, provide therapeutic electrical stimulation to a heart of a patient via electrodes of one or more implantable leads. The therapeutic electrical stimulation may be delivered to the heart in the form of pulses or shocks for pacing, cardioversion or defibrillation. In some cases, an implantable medical device may sense intrinsic depolarizations of the heart, and control the delivery of therapeutic stimulation to the heart based on the sensing.

Cardiac resynchronization therapy is one type of therapy delivered by an implantable medical device. Cardiac resynchronization therapy may help enhance cardiac output by resynchronizing the electromechanical activity of the ventricles of the heart. Ventricular desynchrony may occur in patients that suffer from congestive heart failure (CHF). A number of pacing therapies, such as biventricular pacing and fusion pacing, have been advanced for improving coordination of ventricular contractions.

SUMMARY

In general, the disclosure is directed to adjusting pacing therapy based on ventriculo-atrial delay in order to control ventricular filling times during the delivery of pacing therapy by an implantable medical device (IMD). The ventriculo-atrial delay may be, for example, an interval of time between a ventricular pace event and a subsequent atrial pace or sensing event. The techniques described herein may particularly useful in pacing systems that provide cardiac resynchronization therapy (CRT) to a patient that is experiencing irregular ventricular depolarization due to ventricular dysfunction or ventricular asynchrony. Some types of cardiac resynchronization therapy prolong the electrical activation sequence of the heart and lead to decreased ventricular filling times. In accordance with the techniques described herein, one or more aspects of cardiac pacing therapy (e.g., a pacing rate, pre-excitation interval or a type of pacing therapy) are adjusted in order to maintain adequate ventricular filling times during the delivery of such therapies.

In some examples, the pacing therapy delivered by the IMD is adjusted in order to compensate for decreased ventricular filling time when a ventriculo-atrial delay interval is less than a threshold. In additional examples, the pacing therapy is adjusted in order to compensate for increased ventricular filling time when the ventriculo-atrial delay interval greater than or equal to the threshold.

In one aspect, the disclosure is directed to a method comprising delivering pacing therapy to a ventricular chamber with an implantable medical device, determining a ventriculo-atrial delay interval for the ventricular chamber for at least one cardiac cycle, determining whether the ventriculo-atrial delay interval is less than or equal to a threshold, and adjusting the pacing therapy delivered by the implantable medical device when the ventriculo-atrial delay interval is less than or equal to the threshold.

In another aspect, the disclosure is directed to a system comprising a signal generator that generates and delivers pacing therapy to a ventricular chamber, and a processor that determines a ventriculo-atrial delay interval for the ventricular chamber for at least one cardiac cycle, determines whether the ventriculo-atrial delay interval is less than or equal to a threshold, and adjusts the pacing therapy by the signal generator when the ventriculo-atrial delay interval is less than or equal to the threshold.

In another aspect, the disclosure is directed to a system comprising means for delivering pacing therapy to a ventricular chamber with an implantable medical device, means for determining a ventriculo-atrial delay interval for the ventricular chamber for at least one cardiac cycle, means for determining whether the ventriculo-atrial delay interval is less than or equal to a threshold, and means for adjusting the pacing therapy delivered by the implantable medical device when the ventriculo-atrial delay interval is less than or equal to the threshold.

In another aspect, the disclosure is directed to a computer-readable medium comprising instructions that cause a processor to control a signal generator of an implantable medical device to deliver pacing therapy to a ventricular chamber with an implantable medical device, determine a ventriculo-atrial delay interval for the ventricular chamber for at least one cardiac cycle, determine whether the ventriculo-atrial delay interval is less than or equal to a threshold, and adjust the pacing therapy delivered by the signal generator when the ventriculo-atrial delay interval is less than or equal to the threshold.

In another aspect, the disclosure is directed to a computer-readable medium comprising instructions that cause a processor to perform any part of the techniques described herein.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
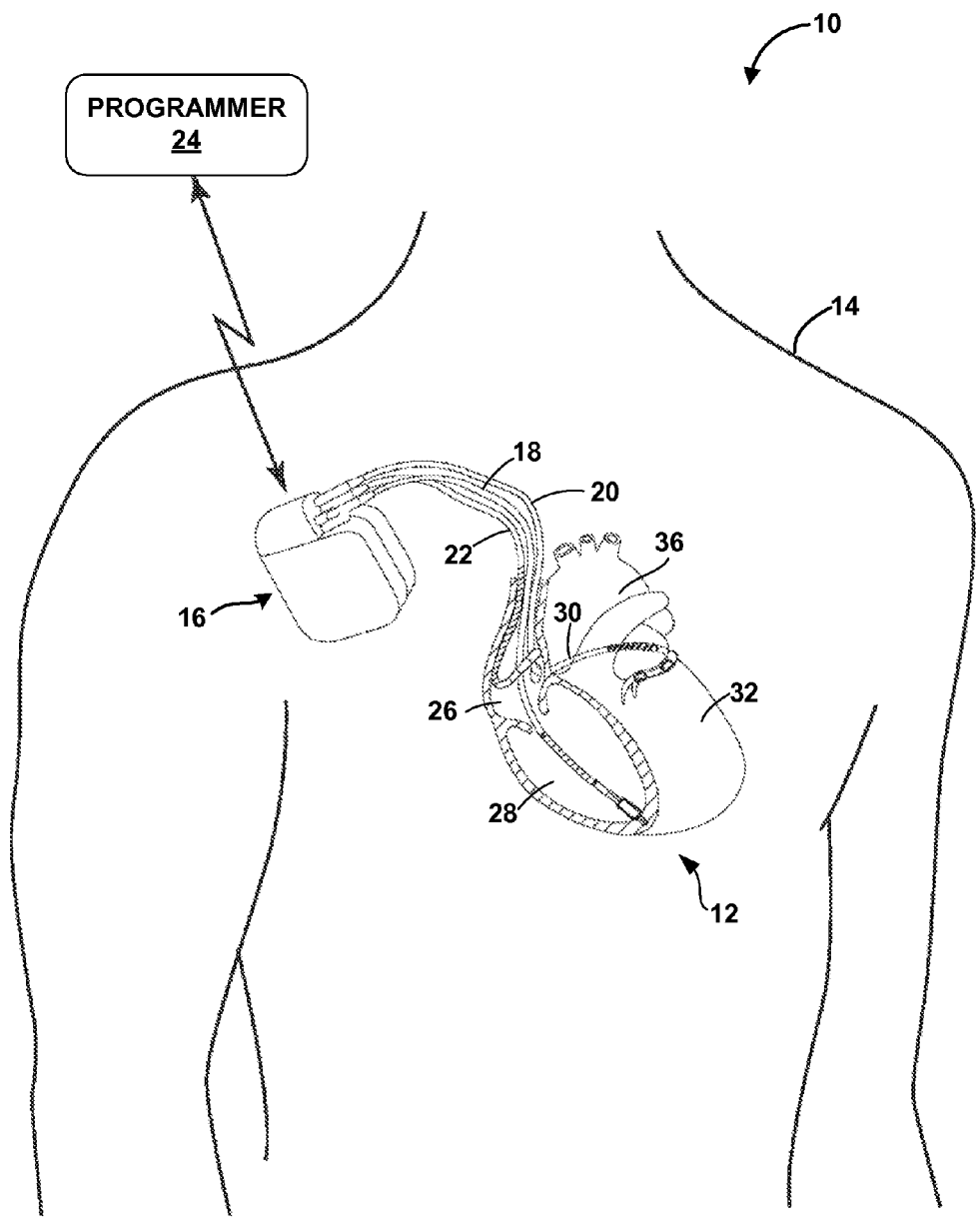
FIG. 1 is a conceptual diagram illustrating an example therapy system comprising an implantable medical device (IMD) for delivering stimulation therapy to a heart of a patient via implantable leads.

Systems, devices, and techniques for adjusting pacing therapy to maintain a suitable ventricular filling time are described herein. In accordance with the techniques described herein, a ventricular filling time interval of a heart is based on a determined ventriculo-atrial time interval (V-A) for a ventricular chamber receiving pacing stimuli. In some examples, the ventriculo-atrial delay interval is the interval of time between a ventricular pace event and a subsequent atrial pace or sensing event ($A_{P/S}$). As described in further detail below, e.g., with respect to FIG. 7, the pacing therapy may be adjusted upon determining a ventriculo-atrial delay interval for one or more cardiac cycles is less than or equal to a predetermined threshold value. In some examples, the threshold value is about 300 milliseconds (ms) to about 400 ms, such as about 350 ms. However, the threshold value may change, e.g., based on whether the patient is an adult or a child.

The techniques described herein for adjusting pacing therapy to maintain a suitable ventricular filling time may particularly useful in pacing systems that provide cardiac resynchronization therapy (CRT) to a patient who is experiencing irregular ventricular depolarization due to ventricular dysfunction or ventricular asynchrony. In patients with ventricular asynchrony, one ventricle may intrinsically depolarize prior to the intrinsic depolarization of the other ventricle. An intrinsic depolarization may refer to a ventricular depolarization that naturally occurs without the use of ventricular pacing delivered by an implantable medical device (IMD).

Some types of CRT, such as fusion-based cardiac resynchronization therapy, may prolong the electrical activation sequence of the heart and lead to decreased ventricular filling times. In accordance with the techniques described herein, cardiac pacing therapy is adjusted in order to maintain a desirable ventricular filling times during the delivery of CRT. It is desirable to maintain a sufficient filling time of a heart of a patient in order to maintain a sufficient level of cardiac output of the heart. Ventricular filling time may determine the amount of blood that is expelled from the atria and/or ventricles of the heart in a subsequent cardiac cycle. If the ventricular filling time is insufficient, the heart may be unable to deliver blood to the patient's body, e.g., to supply sufficient cardiac output to the peripheral tissues to meet metabolic demands of the patient's body.

Fusion-based cardiac resynchronization therapy is useful for restoring a depolarization sequence of a heart of a patient, which may be irregular due to ventricular dysfunction. The delivery of a pacing stimulus (e.g., pulse) to a later depolarizing ventricle (V2) is timed such that an evoked depolarization of the V2 is effected in fusion with the intrinsic depolarization of the first depolarizing ventricle (V1), resulting in a ventricular resynchronization. In this way, the V2 pacing pulse ($V_{2P}$) may pre-excite the conduction delayed V2 and help fuse the activation of the V2 with the activation of the V1 from intrinsic conduction. Thus, the pacing therapy described herein may be referred to as pre-excitation fusion pacing therapy or fusion pacing therapy.

In some fusion pacing techniques, the pacing pulse to a later depolarizing ventricle (V2) is delivered upon expiration of a pacing interval that is determined based on the intrinsic depolarization of the V1. An example of an existing fusion pacing technique that times the delivery of the V2 pacing pulse ($V2_P$) to the intrinsic depolarization of the V1 is described in U.S. Pat. No. 7,181,284 to Burnes et al., which is entitled, "APPARATUS AND METHODS OF ENERGY EFFICIENT, ATRIAL-BASED BIVENTRICULAR FUSION-PACING," and issued on Feb. 20, 2007. U.S. Pat. No. 7,181,284 to Burnes et al. is incorporated herein by reference in its entirety. In some examples, the pacing interval for fusion pacing is the interval of time between an atrial sensing or pace event ($A_{P/S}$) and the delivery of the V2 pacing pulse ($V2_P$).

In some examples, such as the example described in U.S. Pat. No. 7,181,284 to Burnes et al., the pacing interval is determined to be the duration of time between an atrial sensing or pace event ($A_{P/S}$) and a V1 sensing event ($VS_1$) of the same cardiac cycle, decremented by a pre-excitation interval. The PEI may indicate the amount of time with which a V2 pulse precedes a V1 sensing event in order to achieve the fusing of the electromechanical performance of the V1 and V2. That is, the PEI may indicate the amount of time from the delivery of the V2 pacing pulse that is required to pre-excite the V2, such that the electromechanical performance of V1 and V2 merge into a fusion event. A cardiac cycle may refer to a time period between successive atrial pacing or sensing events ($A_{P/S}$).

In some examples, the right ventricle (RV) is the V1 and the left ventricle (LV) is the V2. While the disclosure primarily refers examples in which the first depolarizing ventricle V1 is the RV and the later depolarizing ventricle V2 is the LV, the techniques described herein for providing fusion-based cardiac resynchronization therapy may also apply to examples in which the first depolarizing ventricle V1 is the LV and the later depolarizing ventricle V2 is the RV.

FIG. 1 is a conceptual diagram illustrating an example therapy system 10 that may be used to provide therapy to heart 12 of patient 14. Patient 14 is ordinarily, but not necessarily, a human patient. Therapy system 10 includes IMD 16, which is coupled to leads 18, 20, and 22, and programmer 24. IMD 16 may be, for example, a device that provides cardiac rhythm management therapy to heart 12, and may include, for example, an implantable pacemaker, cardioverter, and/or defibrillator that provide therapy to heart 12 of patient 14 via electrodes coupled to one or more of leads 18, 20, and 22. In some examples, IMD 16 may deliver pacing pulses, but not cardioversion or defibrillation pulses, while in other examples, IMD 16 may deliver cardioversion and/or defibrillation pulses in addition to pacing pulses.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into right atrium 26 of heart 12. In other examples, therapy system 10 may include an additional lead or lead segment (not shown in FIG. 1) that deploys one or more electrodes within the vena cava or other vein.

These electrodes may allow alternative electrical sensing configurations that may provide improved sensing accuracy in some patients.

IMD 16 senses electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. These electrical signals sensed within heart 12 may also be referred to as cardiac signals or electrical cardiac signals. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver cardioversion or defibrillation therapy to heart 12 in the form of electrical pulses. In some examples, IMD 16 may be programmed to deliver a progression of therapies, e.g., pulses with increasing energy levels, until a tachyarrhythmia of heart 12 is stopped. IMD 16 detects tachycardia or fibrillation employing one or more tachycardia or fibrillation detection techniques known in the art.

IMD 16 includes a fusion pacing mode during which IMD 16 delivers a pacing stimulus (e.g., a pacing pulse) to LV 32 via electrodes of lead 20, where the pacing stimulus is timed such that an evoked depolarization of LV 32 is effected in fusion with the intrinsic depolarization of RV 28, resulting in a ventricular resynchronization. In this way, the pacing pulse delivered to LV 32 ($LV_P$) may pre-excite a conduction delayed LV 32 and help fuse the activation of LV 32 with the activation of RV 28 from intrinsic conduction. The fusion of the depolarization of LV 32 and RV 28 may result in synchronous activation and contraction of LV 32 with RV 28. In some examples of the fusion pacing mode, IMD 16 delivers a single ventricular stimulus per cardiac cycle, although any suitable number of pacing stimuli per cardiac cycle is contemplated.

In some examples, IMD 16 times the delivery of the LV pacing pulse to occur at a time relative to the intrinsic RV 28 activation. The fusion depolarization of LV 32 is attained by timing the delivery of the LV pacing pulse ($LV_P$) to follow the intrinsic depolarization of RV 28, but to precede the intrinsic depolarization of LV 32. Specifically, in the fusion pacing mode, IMD 16 does not deliver an RV pacing pulse ($RV_P$), allowing natural propagation of the wave front and depolarization of the intraventricular septum, while an LV pacing pulse ($LV_P$) is delivered in fusion with the intrinsic depolarization of RV 28. In other examples, an RV pacing pulse ($RV_P$) may be delivered in fusion with an intrinsic LV depolarization in cases where the RV is the second-to-depolarize ventricle.

IMD 16 may also include a biventricular pacing mode during which IMD 16 delivers pacing stimuli to both RV 28 and LV 32 via electrodes of the respective leads 18, 20. IMD 16 may provide biventricular pacing therapy by delivering pacing stimuli (e.g., stimulation pulses) to both RV 28 and LV 32 either simultaneously or separated by a programmable interventricular (V-V) pace delay. The V-V pace delay may be either an RV-LV pace delay or an LV-RV pace delay depending on the order of intrinsic depolarization of the ventricles. In one example, IMD 16 times the delivery of a first ventricular pacing event to a first ventricle to an atrial sensing or pace event (AP/S), and times the delivery of a second ventricular pacing event to the second ventricle to the delivery of the first ventricular pacing stimulus or to a ventricular sensing event in the first ventricle.

In another example, IMD 16 utilizes an A-RV delay timer and an A-LV delay timer to time the delivery of the pacing stimuli to RV 28 and LV 32. For example, IMD 16 may begin the A-RV delay timer and an A-LV delay timer when either an atrial pace or sensing event occurs ($A_{P/S}$) and deliver the right ventricular pacing pulse ($RV_P$) and the left ventricular pacing pulse ($LV_P$) are delivered to the RV 28 and LV 32, respectively, upon expiration of the respective timers.

IMD 16 may provide CRT via the fusion pacing mode and/or biventricular pacing mode. CRT provided by IMD 16 may be useful for maintaining the cardiac rhythm in patient 14 with a conduction dysfunction, which may result when the natural electrical activation system of heart 12 is disrupted. The natural electrical activation system of a human heart 12 involves several sequential conduction pathways starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and a final distribution to the distal myocardial terminals via the Purkinje fiber network.

In a normal electrical activation sequence, the cardiac cycle commences with the generation of a depolarization wave at the SA Node in the wall of RA 26. The depolarization wave is transmitted through the atrial conduction pathways of Bachmann's Bundle and the Internodal Tracts at the atrial level into the left atrial septum. When the atrial depolarization wave has reached the AV node, the atrial septum, and the furthest walls of the right and left atria 26, 36, respectively, the atria 26, 36 may contract as a result of the electrical activation. The aggregate right atrial and left atrial depolarization wave appears as the P-wave of the PQRST complex of an electrical cardiac signal, such as a cardiac electrogram (EGM) or electrocardiogram (ECG). When the amplitude of the atrial depolarization wave passing between a pair of unipolar or bipolar pace/sense electrodes located on or adjacent RA 26 and/or LA 36 exceeds a threshold, it is detected as a sensed P-wave. The sensed P-wave may also be referred to as an atrial sensing event, or an RA sensing event ($RA_S$). Similarly, a P-wave sensed in the LA 36 may be referred to as an atrial sensing event or an LA sensing event ($LA_S$).

During or after the atrial contractions, the AV node distributes the depolarization wave inferiorly down the Bundle of His in the intraventricular septum. The depolarization wave may travel to the apical region of heart 12 and then superiorly though the Purkinje Fiber network. The aggregate right ventricular and left ventricular depolarization wave and the subsequent T-wave accompanying re-polarization of the depolarized myocardium may appear as the QRST portion of the PQRST cardiac cycle complex. When the amplitude of the QRS ventricular depolarization wave passing between a bipolar or unipolar pace/sense electrode pair located on or adjacent RV 28 and/or LV 32 exceeds a threshold, it is detected as a sensed R-wave. The sensed R-wave may also be referred to as a ventricular sensing event, an RV sensing event ($RV_S$), or an LV sensing event ($LV_S$) depending upon which ventricle the electrodes of one or more of leads 18, 20, 22 are configured to sense in a particular case.

Some patients, such as patients with congestive heart failure (CHF) or cardiomyopathies, may have left ventricular dysfunction, whereby the normal electrical activation sequence through heart 12 is compromised within LV 32. Congestive heart failure is defined generally as the inability of the heart to deliver enough blood, e.g., to supply sufficient cardiac output, to the peripheral tissues to meet metabolic demands. In a patient with left ventricular dysfunction, the normal electrical activation sequence through heart 12 becomes disrupted. For example, patients may experience an intra-atrial conduction defect, such as intra-atrial block. Intra-atrial block is a condition in which the atrial activation is delayed because of conduction delays between RA 26 to LA 36.

As another example, a patient with left ventricular dysfunction may experience an intraventricular conduction defect, such as left bundle branch block (LBBB) and/or right bundle branch block (RBBB). In LBBB and RBBB, the activation signals are not conducted in a normal fashion along the right or left bundle branches respectively. Thus, in patients with bundle branch block, the activation of either RV 28 or LV 32 is delayed with respect to the other ventricle, causing asynchrony between the depolarization of the right and left ventricles 28, 32, respectively. Ventricular asynchrony may be identified by a widened QRS complex due to the increased time for the activation to traverse the ventricular conduction paths. The asynchrony may result from conduction defects along the Bundle of His, the Right and Left Bundle Branches or at the more distal Purkinje Terminals. Typical intra-ventricular peak-to-peak asynchrony can range from about 80 ms to about 200 ms or longer. However, in patients who are experiencing RBBB and LBBB, the QRS complex may be widened far beyond the normal range to a wider range, e.g., about 120 ms to about 250 ms or greater.

CRT delivered by IMD 16, in either the fusion pacing mode or the biventricular pacing mode, may help alleviate heart failure conditions by restoring synchronous depolarization and contraction of one or more chambers of heart 12. In some cases, the CRT described herein enhances stroke volume of a patient by improving the synchrony with which RV 28 and LV 32 depolarize and contract. As previously indicated, IMD 16 may deliver therapy to patient 14 upon expiration of a pacing interval, which beings upon detection of an atrial sensing or pace event ($A_{P/S}$). Thus, the pacing interval for some fusion pacing examples may be the interval of time between an atrial sensing or pace event ($A_{P/S}$) and the delivery of the V2 pacing pulse ($V2_P$). In some examples, the pacing interval for a fusion pacing mode of IMD 16, also referred to as the $A_{P/S}$-$LV_P$ delay or the $A_{P/S}$-$LV_P$ interval, is determined to be:

$$A_{P/S}\text{-}LV_P \text{ delay}=(A_{P/S}\text{-}RV_S)-\text{PEI} \quad (1)$$

Ventricles 28, 32 of heart 12 may fill during an interval of time between the delivery of the LV 32 pacing pulse ($LV_P$) and a subsequent atrial sensing or pace event ($A_{P/S}$). This interval of time may be referred to as a ventriculo-atrial delay interval. The filling time of ventricles 28, 32 of heart 12 decreases as the ventriculo-atrial delay interval decreases. The ventriculo-atrial delay interval may decrease as the time interval between subsequent atrial sensing or pace events decreases ($A_{P/S}$-$A_{P/S}$), which may occur as a heart rate of patient 14 increases. In addition, the ventriculo-atrial delay interval may decrease as the pacing interval ($A_{P/S}$-$LV_P$ delay from Equation 1) increases.

IMD 16 adjusts pacing therapy based on a determined ventriculo-atrial delay interval in order to maintain the ventriculo-atrial delay interval (e.g., $LV_P$-$A_{P/S}$) at or above a threshold value. The ventriculo-atrial delay interval may be indicative of a ventricular filling time during a cardiac cycle. Accordingly, maintaining the ventriculo-atrial delay interval at or above a threshold value may help maintain the ventricular filling time of a cardiac cycle at or above a threshold level. In some examples, the threshold level may be predetermined and correspond to a physiologically significant fill time, which may be the fill time required for heart 12 to provide sufficient cardiac output (e.g., sufficient blood flow) to meet the needs of the patient's body.

As previously indicated, some types of CRT, such as fusion-based cardiac resynchronization therapy, may prolong the electrical activation sequence of the heart and lead to decreased ventricular filling times. In some examples, IMD 16 adjusts the pacing rate of the in order to compensate for a decrease in the ventriculo-atrial delay interval, which indicates a decrease in the decreased ventricular filling time. In additional examples, IMD 16 may adjust a PEI for pacing of the ventricular chamber in order to compensate for a decrease in the ventriculo-atrial delay interval. In further examples, IMD 16 may switch between a fusion pacing mode and a biventricular pacing mode, or vice-versa, in order to compensate for a decrease in the ventriculo-atrial delay interval.

In some examples described herein (e.g., with respect to FIG. 7), pacing therapy delivered by IMD 16 is adjusted in order to compensate for decreased ventricular filling time when a ventriculo-atrial delay interval is less than a threshold. In some cases, the pacing therapy may also be adjusted in order to compensate for increased ventricular filling time when the ventriculo-atrial delay interval greater than or equal to the threshold. Thus, according to some techniques described herein, IMD 16 delivers fusion pacing therapy to patient 14 as long as the ventricular filling times are within acceptable limits. If ventricular filling times deviate from acceptable levels or are about to deviate from acceptable levels, the techniques in this disclosure provide for the adjustment of pacing therapy in order to preserve or return the ventricular filling times to appropriate levels. Thus, the techniques in this disclosure allow IMD 16 to harness the power savings and/or increased effectiveness of fusion pacing in cases where prolongation of the activation sequence may normally impair the use of fusion pacing therapy because of a decrease in ventricular filling time.

The techniques described herein may be used to control a ventricular filling time interval of a heart based on a measured and/or derived ventriculo-atrial delay interval (V-A). The ventriculo-atrial delay interval may refer to a time interval between a pacing event for a second-to-depolarize ventricle, which is LV 32 in the example shown in FIG. 1, and ending with either an atrial sensing event or an atrial pacing event ($A_{P/S}$) for either of RA 26 or LA 36. While the ventriculo-atrial delay interval is primarily referred to as the $V2_P$-$A_{P/S}$ interval in the description, in other examples, RV 28 may be a later-depolarizing ventricle. In such examples, the ventriculo-atrial delay interval may be referred to as the $V1_P$-$A_{P/S}$ interval.

In some examples, the ventriculo-atrial delay interval ($LV_P$-$A_{P/S}$) is directly determined by evaluating the interval of time between the V2 pacing pulse and the subsequent atrial pacing event ($A_{P/S}$). In additional examples, the ventriculo-atrial delay interval ($LV_S$-$A_{P/S}$) may be based on a determined atrio-ventricular delay interval for a first-to-depolarize ventricular chamber ($A_{P/S}$-$V1_S$). In particular, in some examples, IMD 16 or another device determines the ventriculo-atrial delay interval ($LV_S$-$A_{P/S}$) by determining the interval of time between subsequent atrial sensing or pace events ($A_{P/S}$-$A_{P/S}$) decremented by the pacing interval, as shown in Equation 2:

$$LV_P\text{-}A_{P/S} \text{ interval}=(A_{P/S}\text{-}A_{P/S})-[(A_{P/S}\text{-}RV_S)-\text{PEI}] \quad (2)$$

The determination of the ventriculo-atrial delay interval ($LV_P$-$A_{P/S}$) may, in some cases, require the suspension of pacing therapy to one or more ventricles 28, 32. Many existing fusion pacing therapy systems are configured to periodically suspend ventricular pacing based on an AV evaluation interval timer in order to periodically update the ventricular pacing interval. Thus, the measurement and calculation techniques described herein may be able to utilize the same timing cycle used for suspension of ventricular pacing therapy and/or switching from a fusion pacing mode to a biventricular pacing mode (which may include a fixed A-V delay that allows a prolonged and subsequently fixed V-A interval to prolong filling times) as already used in fusion pacing therapy systems in order to determine the ventriculo-atrial delay interval ($LV_P$-$A_{P/S}$).

The techniques implemented by IMD 16 to control fusion pacing therapy may provide one or more advantages over existing techniques for CRT. As opposed to existing techniques, which use indirect determinations of ventricular fill time as surrogates for ventricular filling time, the techniques in this disclosure provide a metric that directly corresponds to a portion of the cardiac cycle during which the ventricular filling actually takes place. The use of a direct metric, as opposed to an indirect surrogate, provides a more robust measurement than the prior indirect measurements of ventricular fill time. The direct metric for determining ventricular filling time may be more indicative of variations in the ventricular filling time that may not be detected by indirect measurements.

As another example, the techniques of this disclosure may allow, in some examples, for the calculation of a ventricular filling time metric based on existing measures of cardiac activation, such as, for example, a heart rate measurement or an intrinsic atrio-ventricular delay measurement. In other examples, the techniques of this disclosure may allow for the calculation of a ventricular filling time metric based on existing mechanical measurement techniques (e.g., pressure sensors, blood flow sensors, accelerometers), existing chemical measurements (e.g., blood metabolites), and/or based on temperature. Because fusion pacing therapy systems may already perform one or more of these measurements, the techniques described herein may be able to be easily incorporated into measurement infrastructures that are already in-use by existing fusion pacing therapy systems.

In some examples, programmer 24 may be a handheld computing device, computer workstation, or networked computing device. Programmer 24 includes a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display. It should be noted that the user may also interact with programmer 24 or IMD 16 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as electrical depolarization/repolarization signals from the heart (referred to as "electrogram" or EGM), intracardiac or intravascular pressure, activity, posture, respiration, heart rate, heart sounds, or thoracic impedance. As another example, the user may use programmer 24 to retrieve information from IMD 16 regarding the performance or integrity of IMD 16 or other components of system 10, such as leads 18, 20 and 22, or a power source of IMD 16.

The user may use programmer 24 to program a therapy progression, select electrodes used to deliver defibrillation pulses, select waveforms for the defibrillation pulses, or select or configure a fibrillation detection algorithm for IMD 16. The user may also use programmer 24 to program similar aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
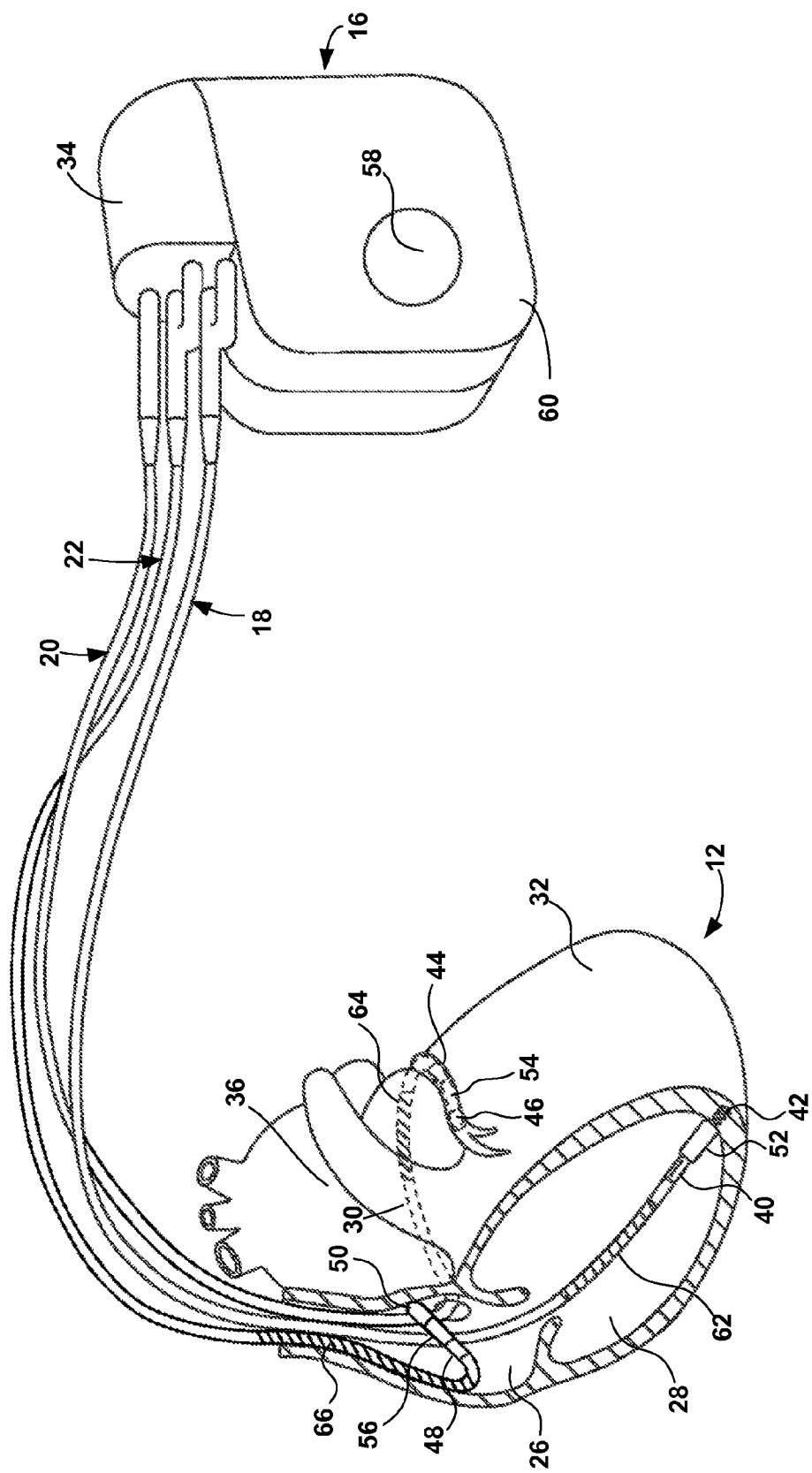
FIG. 2 is a conceptual diagram further illustrating the IMD and leads of the system of FIG. 1 in greater detail.

FIG. 2 is a conceptual diagram illustrating a three-lead IMD 16 and leads 18, 20 and 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Other lead configurations are also contemplated, such as configurations that do not include coiled conductors. In the illustrated example, bipolar electrodes 40 and 42 are located proximate to a distal end of lead 18 in RV 28. In addition, bipolar electrodes 44 and 46 are located proximate to a distal end of lead 20 in LV 32 and bipolar electrodes 48 and 50 are located proximate to a distal end of lead 22 in RA 26. Although no electrodes are located in LA 36 in the illustrated example, other examples may include electrodes in LA 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the conductors within the lead body of its associated lead 18, 20, 22, and thereby coupled to respective ones of the electrical contacts on the proximal end of leads 18, 20, 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other divisions between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor couple to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

Any multipolar combination of two or more of electrodes 40, 42, 44, 46, 48, 50, 58, 62, 64, and 66 may be considered a sensing electrode configuration. Usually, but not necessarily, a sensing electrode configuration is a bipolar electrode combination on the same lead, such as electrodes 40 and 42 of lead 18. On one lead having three electrodes, there may be at least three different sensing electrode configurations available to IMD 16. These sensing electrode configurations are, for the example of lead 18, tip electrode 42 and ring electrode 40, tip electrode 42 and elongated electrode 62, and ring electrode 40 and elongated electrode 62. However, some examples may utilize sensing electrode configurations having electrodes of two different leads. Further, a sensing electrode configuration may utilize housing electrode 58, which may provide a unipolar sensing electrode configuration. In some examples, a sensing electrode configuration may comprise multiple housing electrodes 58. In any sensing electrode configuration, the polarity of each electrode in the may be configured as appropriate for the application of the sensing electrode configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
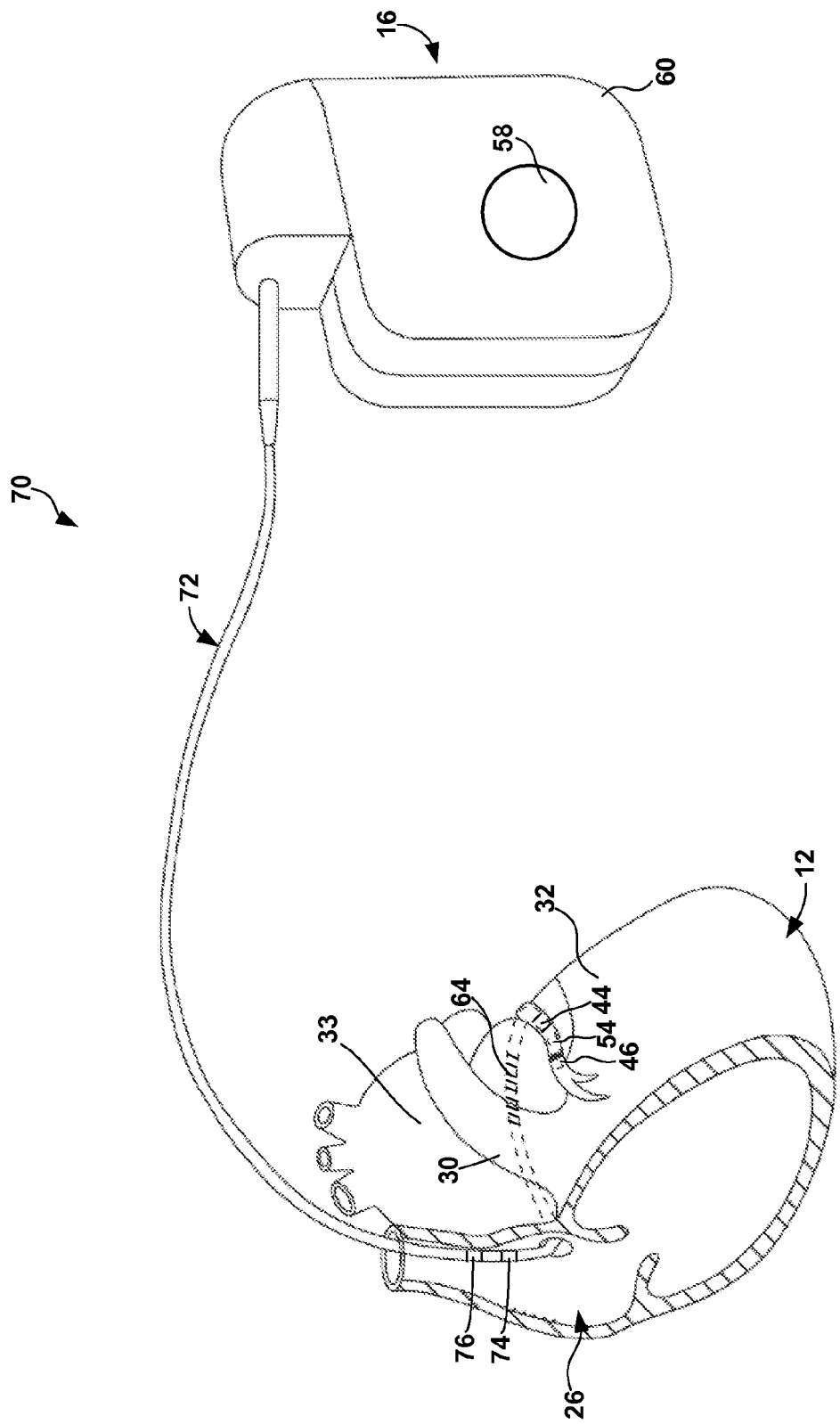
FIG. 3 is a conceptual diagram illustrating another example therapy system comprising the IMD of FIG. 1 coupled to a different configuration of leads.

In other examples of therapy systems that provide electrical stimulation therapy to heart 12, a therapy system may include any suitable number of leads coupled to IMD 16, and each of the leads may extend to any location within or proximate to heart 12. For example, a therapy system may include a single chamber or dual chamber device rather than a three-chamber device as shown in FIG. 1. In a single chamber configuration, IMD 16 is electrically connected to a single lead 20 that includes stimulation and sense electrodes within LV 32. In one example of a dual chamber configuration, IMD 16 is electrically connected to a single lead that includes stimulation and sense electrodes within LV 32 as well as sense and/or stimulation electrodes within RA 26, as shown in FIG. 3. In another example of a dual chamber configuration, IMD 16 is connected to two leads that extend into a respective one of the RA 28 and LV 32. Other lead configurations are contemplated.

FIG. 3 is a conceptual diagram illustrating another example therapy system 70, which is similar to therapy system 10 of FIGS. 1-2, but includes a single lead 72, rather than three leads. Lead 72 is implanted within LV 32 and RA 26. Lead 72 is similar to lead 20 of FIG. 2, but includes electrodes 74, 76 within RA 26 to sense electrical activity of RA 26 (e.g., P-waves). Therapy system 70 shown in FIG. 4 may be useful for providing pacing pulses to LV 32 of heart 12 in accordance with the fusion-based cardiac resynchronization techniques described herein. While the description of FIGS. 7-10 primarily refers to therapy system 10 of FIG. 2, the devices, systems, and techniques described herein may also be used to implement therapy delivery by therapy system 70.

Figure 4:
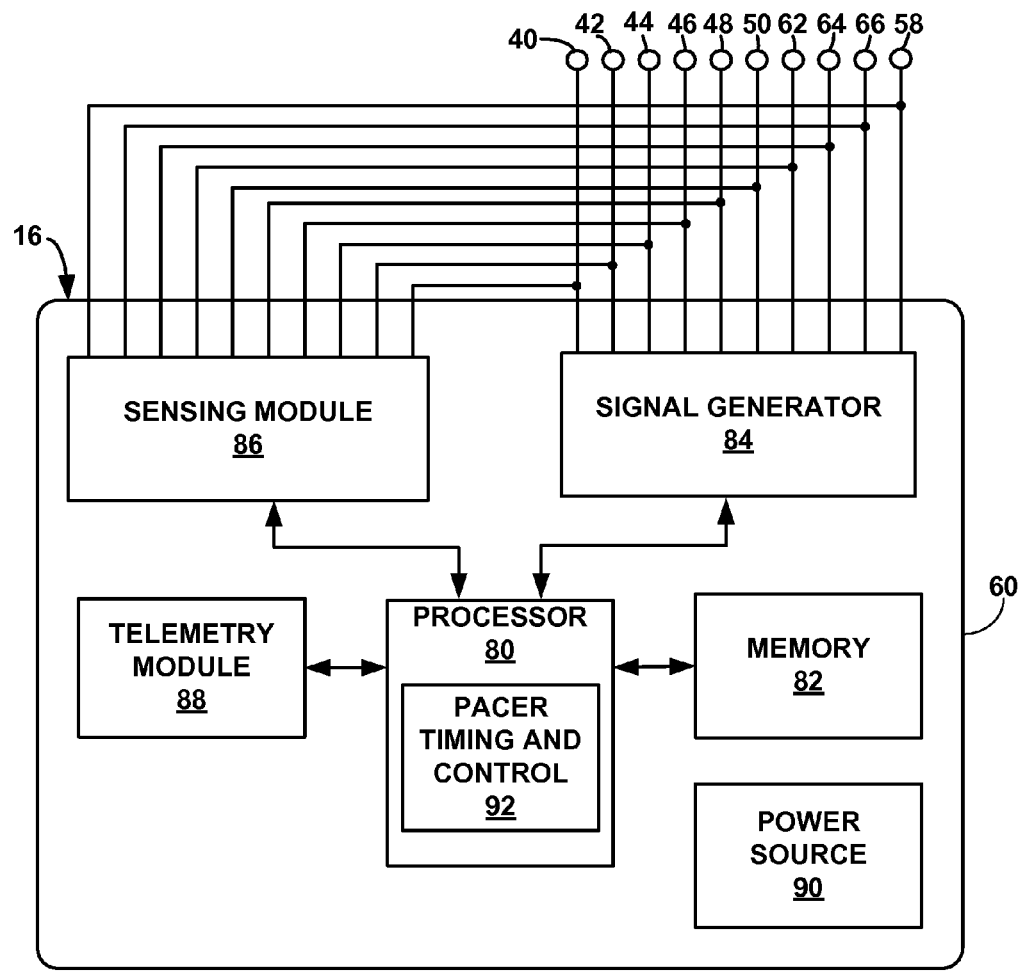
FIG. 4 is a functional block diagram illustrating an example configuration of the IMD of FIG. 1.

FIG. 4 is a functional block diagram illustrating an example configuration of IMD 16. In the example illustrated by FIG. 4, IMD 16 includes a processor 80, memory 82, signal generator 84, electrical sensing module 86, telemetry module 88, and power source 90. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12. Processor 80 may control signal generator 84 to deliver stimulation according to a selected one or more therapy programs, which may be stored in memory 82. For example, processor 80 may control signal generator 84 to deliver electrical pulses with the amplitudes, pulse widths, frequencies, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. For example, signal generator 84 may deliver a pacing stimulus to LV 32 (FIG. 2) of heart 12 in accordance with the fusion pacing techniques described herein heart 12 via at least two electrodes 44, 46 (FIG. 2). As another example, signal generator 84 may deliver defibrillation shocks to heart 12 via at least two electrodes 58, 62, 64, 66. In some examples, signal generator 84 delivers pacing, cardioversion, or defibrillation stimulation in the form of electrical pulses. In other examples, signal generator 84 may deliver one or more of these types of stimulation in the form of other signals, such as sine waves, square waves, or other substantially continuous time signals.

In some examples, signal generator 84 may include a switch module and processor 80 may use the switch module to select, e.g., via a data/address bus, which of the available electrodes are used to deliver pacing, cardioversion, or defibrillation pulses. The switch module may include a switch array, switch matrix, multiplexer, or any other type of switching device suitable to selectively couple stimulation energy to selected electrodes. In other examples, however, signal generator 94 may independently deliver stimulation to electrodes 40, 42, 44, 46, 48, 50, 58, 62, 64, 66 or selectively sense via one or more of electrodes 40, 42, 44, 46, 48, 50, 58, 62, 64, 66 without a switch matrix.

Sensing module 86 monitors signals from at least one of electrodes 40, 42, 44, 46, 48, 50, 58, 62, 64, 66 in order to monitor electrical activity of heart 12. For example, sensing module 86 may sense atrial events (e.g., a P-wave) with electrodes 48, 50, 66 within RA 26 or sense an LV 32 event (e.g., an R-wave) with electrodes 44, 46, 64 within LV 32. Sensing module 86 may also include a switch module to select which of the available electrodes are used to sense the heart activity. In some examples, processor 80 may select the electrodes that function as sense electrodes, or the sensing electrode configuration, via the switch module within electrical sensing module 86, e.g., by providing signals via a data/address bus. In some examples, sensing module 86 may include multiple sensing channels, each of which may comprise an amplifier. In response to the signals from processor 80, the switch module of within sensing module 86 may couple the outputs from the selected electrodes to one or more of the sensing channels.

In some examples, sensing module 86 may include a plurality of channels. One channel of sensing module 86 may include an R-wave amplifier that receives signals from electrodes 40 and 42, which are used for pacing and sensing in RV 28 of heart 12. Another channel may include another R-wave amplifier that receives signals from electrodes 44 and 46, which are used for pacing and sensing proximate to LV 32 of heart 12. In some examples, in one operating mode of sensing module 86, the R-wave amplifiers may take the form of an automatic gain controlled amplifier that provides an adjustable sensing threshold as a function of the measured R-wave amplitude of the heart rhythm.

In addition, in some examples, one channel of sensing module 86 may include a P-wave amplifier that receives signals from electrodes 48 and 50, which are used for pacing and sensing in right atrium 26 of heart 12. In some examples, in one operating mode of sensing module 86, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. Processor 80 may employ digital signal analysis techniques to characterize the digitized signals stored in memory 82 to detect and classify the patient's heart rhythm from the electrical signals. Processor 80 may detect and classify the heart rhythm of patient 14 by employing any of the numerous signal processing methodologies known in the art.

Signals generated by sensing module 86 may include, for example: an RA-event signal, which indicates a detection of a P-wave via electrodes implanted within RA 26 (FIG. 1); an LA-event signal, which indicates a detection of a P-wave via electrodes implanted within LA 33 (FIG. 1); an RV-event signal, which indicates a detection of an R-wave via electrodes implanted within RV 28; or an LV-event signal, which indicates a detection of an R-wave via electrodes implanted within LV 32. In the example of therapy systems 10, 70 shown in FIGS. 2 and 3, IMD 16 is not connected to electrodes that are implanted within LA 33. However, in other example therapy systems, IMD 16 may be connected to electrodes that are implanted within LA 33 in order to sense electrical activity of LA 33.

Processor 80 may define variable delay intervals that correspond to intrinsic depolarization characteristics of heart 12 based on signals from sensing module 86. These intervals may include, for example, atrial-ventricular intrinsic depolarization delay intervals for LV 28 and RV 32 (e.g., $A_{P/S}$-$RV_S$ or $A_{P/S}$-$LV_S$ delay intervals), ventriculo-atrial intrinsic depolarization delay intervals for t LV 28 and RV 32 (e.g., $RV_S$-$A_{P/S}$ or $LV_S$-$A_{P/S}$ delay intervals), intrinsic heart rate delay intervals (e.g., $A_{P/S}$-$A_{P/S}$ delay interval), and intrinsic interventricular conduction delay intervals (e.g., $RV_S$-$LV_S$ or $LV_S$-$RV_S$ delay intervals).

Processor 80 may also define variable delay intervals for triggering the delivery of pacing therapy to one or more chambers of heart 12. These intervals may include, for example, a RV pacing interval (e.g., $A_{P/S}$-$RV_P$ delay interval), a LV pacing interval (e.g., $A_{P/S}$-$LV_P$ delay interval), and an atrial pacing interval (e.g., $A_P$-$A_P$ delay interval). The atrial pacing delay interval may also be indicative of the heart rate. The atrial sensing events ($A_S$), pacing events ($A_P$), and delay intervals ($A_{P/S}$-$A_{P/S}$) described in this disclosure may refer to either right atrial sensing events, pacing events, and delay intervals or left atrial sensing events, pacing events, and delay intervals.

In addition, processor 80 may determine other pacing variables to assist in the pacing algorithms described in this disclosure. As one example, processor 80 may define a PEI, which refers to a time interval between a desired time for triggering a pacing event for a second-to-depolarize ventricular chamber within a cardiac cycle and a detected sensing event for a first-to-depolarize ventricular chamber within the cardiac cycle (e.g., $LV_P$-$RV_S$ or $RV_P$-$LV_S$ delay intervals). In other words, the PEI indicates an amount of time prior to the intrinsic depolarization of the first-to-depolarize ventricular chamber at which pacing of the second-to-depolarize ventricular chamber is triggered. The PEI may be programmed to a particular value and/or adjusted such that evoked depolarization of the second-to-depolarize ventricular chamber is effected in fusion with the intrinsic depolarization of the first-to-depolarize ventricular chamber.

In some examples, processor 80 determines an atrio-ventricular evaluation interval (AVEI), which controls when processor 80 performs calibration routines, updates variables, and/or adjusts the pacing therapy delivered. As one example, when the AVEI interval expires, processor 80 may perform an intrinsic atrio-ventricular delay measurement for the first-to-depolarize ventricular chamber. As another example, when the AVEI interval expires, processor 80 may determine a ventriculo-atrial delay interval for a second-to-depolarize ventricular chamber. The AVEI can be based on a programmable number of cardiac cycles (n-beats) and/or a temporal value (n-seconds, n-minutes, etc.).

In some examples, the pacing and intrinsic delay intervals described above are stored within registers or other memory elements within processor 80. In additional examples, the pacing and intrinsic delay intervals are stored in memory 82, which may be accessible by processor 80. In further examples, the pacing and intrinsic delay intervals are stored within registers or interval timers of pacer timing and control unit 92. The pacing and intrinsic delay intervals specified in this disclosure are merely examples of delay intervals that may be defined by processor 80. Other delay intervals pacing and intrinsic delay intervals may be defined without departing from the scope of this disclosure.

Processor 80 may include pacer timing and control module 92, which may include programmable counters and timers in order to assist processor in defining and/or executing the intrinsic and pacing delay intervals described above. Pacer timing and control module 92 may be embodied as hardware, firmware, software, or any combination thereof. Pacer timing and control module 92 may comprise a dedicated hardware circuit, such as an ASIC, separate from other components of processor 80, such as a microprocessor, or a software module executed by a component of processor 80.

Pacer timing and control module 92 may help define the pacing interval (e.g., $A_{P/S}$-$LV_P$ delay) for controlling the delivery of a pacing pulse to LV 32 when IMD 16 operates in a pre-excitation fusion pacing mode. For example, pacing timing and control module 92 may include programmable counters or timers for determining the $A_{P/S}$-$RV_S$ delay and/or any other relevant time intervals. In addition, pacing timing and control module 92 includes timers for timing the delivery of uni-ventricular and/or biventricular pacing stimuli and other functions that are based on the pacing interval.

In examples in which IMD 16 delivers uni-ventricular pacing (e.g., pre-excitation fusion pacing), pacing timing and control module 92 may include a timer that is loaded with the appropriate pacing interval (also referred to as the atrio-ventricular delay) (e.g., $A_{P/S}$-$LV_P$ or $A_{P/S}$-$RV_P$) for the second-to-depolarize ventricular chamber. As previously discussed, the pacing interval for the second-to-depolarize ventricular chamber may be based upon an intrinsic atrio-ventricular depolarization delay (e.g., $A_{P/S}$-$RV_S$ or $A_{P/S}$-$LV_S$) for the first-to-depolarize ventricle and the programmable PEI. For example, in examples in which IMD 16 delivers the LV pacing pulse ($LV_P$) a predetermined period of time following an atrial sensing or pace event ($A_{P/S}$), pacing timing and control module 92 may include a timer that is loaded with the appropriate $A_{P/S}$-$LV_P$ delay. The timer of pacing timing and control module 92 may be configured to begin upon the detection of a preceding atrial pace or sensing event ($A_{P/S}$). Upon expiration of the particular timer, processor 80 may control signal generator 84 to deliver pacing stimulus to the later-depolarizing ventricle (i.e., either LV 32 or RV 28). For example, pacing timing and control module 92 may generate a trigger signal that triggers the output of a pacing pulse by signal generator 84.

In examples in which IMD 16 is configured to deliver other types of cardiac rhythm therapy in addition to pre-excitation fusion pacing, pacer timing and control module 92 may also include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

In examples in which IMD 16 is configured to deliver other types of cardiac rhythm therapy in addition to excitation fusion pacing, intervals defined by pacer timing and control module 92 within processor 80 may include atrial and ventricular pacing escape intervals, refractory periods during which sensed P-waves and R-waves are ineffective to restart timing of the escape intervals, and the pulse widths of the pacing pulses. As another example, pacer timing and control module 92 may define a blanking period, and provide signals from sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within pacer timing and control module 92 of processor 80 may be reset upon sensing of R-waves and P-waves with detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as ventricular fibrillation event or ventricular tachycardia event. Upon detecting a threshold number of tachyarrhythmia events, processor 90 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode.

In some examples, processor 80 may operate as an interrupt driven device that is responsive to interrupts from pacer timing and control module 92, where the interrupts may correspond to the occurrences of sensed P-waves and R-waves and the generation of cardiac pacing pulses. Any necessary mathematical calculations to be performed by processor 80 and any updating of the values or intervals controlled by pacer timing and control module 92 of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998, or in U.S. patent application Ser. No. 10/755,185, filed Jan. 8, 2004 by Kevin T. Ousdigian, entitled "REDUCING INAPPROPRIATE DELIVERY OF THERAPY FOR SUSPECTED NON-LETHAL ARRHYTHMIAS." U.S. Pat. No. 5,545,186 to Olson et al., U.S. Pat. No. 5,755,736 to Gillberg et al., and U.S. patent application Ser. No. 10/755,185 by Kevin T. Ousdigian are incorporated herein by reference in their entireties. However, other arrhythmia detection methodologies may also be employed by processor 80 in other examples.

In the examples described herein, processor 80 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 82 of IMD 16. In addition, the number of tachyarrhythmia events that are detected to confirm the presence of a tachyarrhythmia episode may be stored as a number of intervals to detect (NID) threshold value in memory 82. In some examples, processor 80 may also identify the presence of the tachyarrhythmia episode by detecting a variable coupling interval between the R-waves of the heart signal. For example, if the interval between successive tachyarrhythmia events varies by a particular percentage or the differences between the coupling intervals are higher than a given threshold over a predetermined number of successive cycles, processor 90 may determine that the tachyarrhythmia is present.

In the event that processor 80 detects an atrial or ventricular tachyarrhythmia based on signals from electrical sensing module 86, and an anti-tachyarrhythmia pacing regimen is desired, timing intervals for controlling the generation of anti-tachyarrhythmia pacing therapies by signal generator 84 may be loaded by processor 80 into pacer timing and control module 92 to control the operation of the escape interval counters therein and to define refractory periods during which detection of R-waves and P-waves is ineffective to restart the escape interval counters.

If IMD 16 is configured to generate and deliver defibrillation pulses to heart 12, signal generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachyarrhythmia requiring a cardioversion pulse, processor 80 may activate a cardioversion/defibrillation control module, which may, like pacer timing and control module 92, be a hardware component of processor 80 and/or a firmware or software module executed by one or more hardware components of processor 80. The cardioversion/defibrillation control module may initiate charging of the high voltage capacitors of the high voltage charge circuit of signal generator 84 under control of a high voltage charging control line.

Processor 80 may monitor the voltage on the high voltage capacitor, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of signal generator 84.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., EGM signals) produced by atrial and ventricular sense amp circuits within electrical sensing module 86 to programmer 24. Programmer 24 may interrogate IMD 16 to receive the EGMs. Processor 80 may store EGMs within memory 82, and retrieve stored EGMs from memory 82. Processor 80 may also generate and store marker codes indicative of different cardiac events that electrical sensing module 86 detects, such as ventricular and atrial depolarizations, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis. Examples of a rechargeable battery include, but are not limited to, a lithium ion battery, a lithium polymer battery or a supercapacitor.

Figure 5:
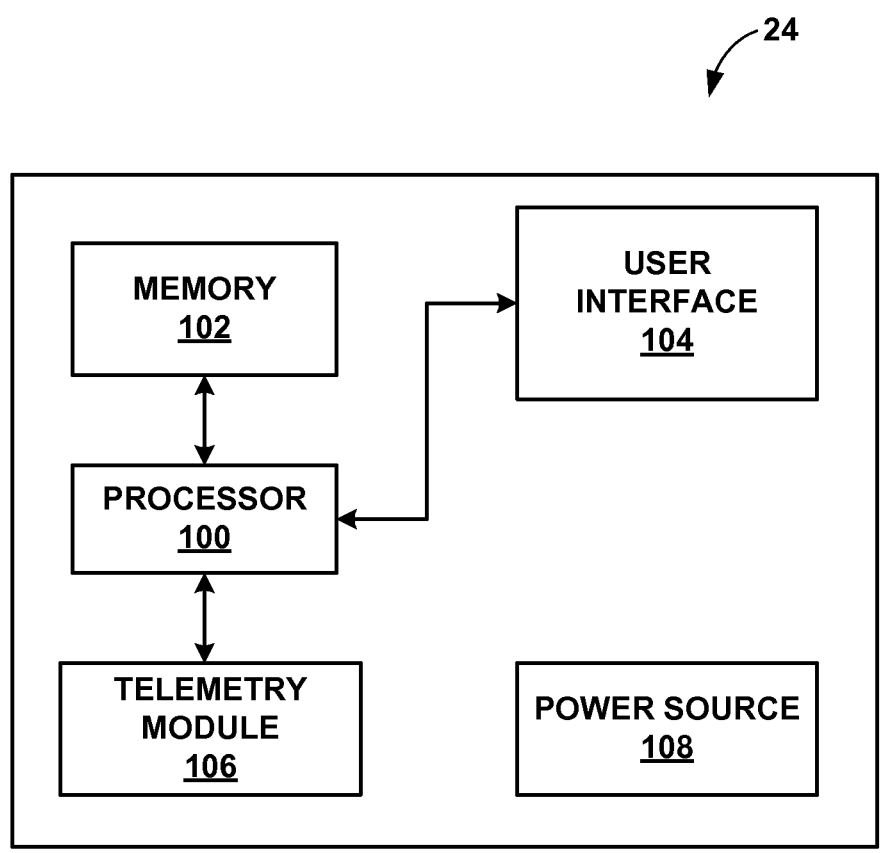
FIG. 5 is a functional block diagram of an example configuration of the external programmer shown in FIG. 1, which facilitates user communication with an IMD.

FIG. 5 is block diagram of an example programmer 24. As shown in FIG. 5, programmer 24 includes processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician interacts with programmer 24 via user interface 104 which may include display to present graphical user interface to a user, and a keypad or another mechanism for receiving input from a user.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Processor 100 of programmer 24 may implement any of the modules depicted in FIG. 5, provide any of the functionality ascribed herein to processor 80 of IMD 16, or otherwise perform any of the methods described herein.

Memory 102 stores instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient. Memory 102 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

Power source 108 delivers operating power to the components of programmer 24. Power source 108 may include a battery and a power generation circuit to produce the operating power. In some examples, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 108 may include circuitry to monitor power remaining within a battery. In this manner, user interface 104 may provide a current battery level indicator or low battery level indicator when the battery needs to be replaced or recharged. In some cases, power source 108 may be capable of estimating the remaining time of operation using the current battery.

Figure 6:
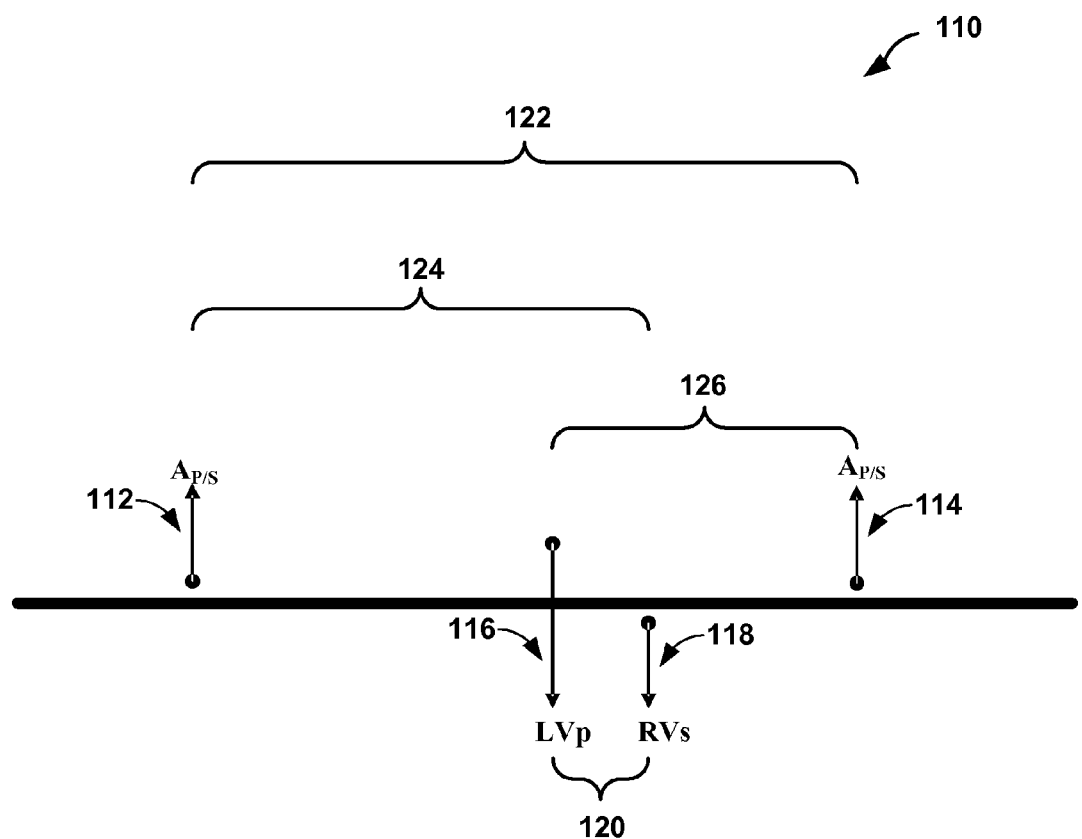
FIG. 6 is a timing diagram illustrating components of a cardiac cycle that may be used when measuring ventriculo-atrial delay.

FIG. 6 is a timing diagram 110 illustrating a cardiac cycle and various segments of the cardiac cycle that may be used to determine ventriculo-atrial delay. The horizontal axis of timing diagram 110 is given in units of time and increases from left to right. The cardiac cycle in timing diagram 110 depicts a single cardiac cycle of uni-ventricular pacing therapy beginning at time marker 112 and ending at time marker 114. At time markers 112 and 114, IMD 16 either delivers an atrial pacing stimulus or senses an atrial event. Hence, time markers 112, 114 correspond to an atrial pace or sensing event ($A_{P/S}$). During the cardiac cycle shown in FIG. 6, which is determined to be between successive atrial pace or sensing events ($A_{P/S}$-$A_{P/S}$), IMD 16 triggers a left ventricular pacing event ($LV_P$) at a time indicated by time marker 116. IMD 16 may detect a right ventricular sensing event ($RV_S$) at time indicated by time marker 118. As depicted in FIG. 6, IMD 16 delivers the LV pacing event ($LV_P$) prior to the occurrence of the RV sensing event ($RV_S$). The time interval between LV pacing event ($LV_P$) at time marker 116 and RV sensing event ($RV_S$) at time marker 118 may be referred to as a PEI 120. PEI 120 may be preprogrammed and/or adjusted such that the evoked depolarization of LV 32 (FIG. 1) is effected in fusion with the intrinsic depolarization of RV 28 (FIG. 1).

Time interval 122 indicates one period of the cardiac cycle. The period of the cardiac cycle is inversely proportional to the heart rate. Time interval 124 indicates an atrio-ventricular delay interval ($A_{P/S}$-$RV_S$) for the first-to-depolarize ventricle (i.e., RV 28 in the example shown in FIG. 6). Time interval 126 represents a ventriculo-atrial delay interval ($LV_P$-$A_{P/S}$) for a second-to-depolarize ventricle (i.e., LV 32 in the example shown in FIG. 6). As previously indicated, in some examples, the ventriculo-atrial delay (generally referred to as V2-A) for the second-to-depolarize ventricle may be determined according to the following equation:

$$V2\text{-}A = (A_{P/S}\text{-}A_{P/S}) - [(A_{P/S}\text{-}V1_S) - \text{PEI}] \quad (3)$$

where V2-A is the ventriculo-delay interval for the second-to-depolarize ventricle and corresponds to time interval 126, ($A_{P/S}$-$A_{P/S}$) is one period of a cardiac cycle represented by time interval 122 in FIG. 6, ($A_{P/S}$-$V1_S$) is an atrial-ventricular delay interval for a first-to-depolarize ventricle (V1) represented by time interval 124, and PEI is the pre-excitation interval represented by time interval 120.

The ventriculo-atrial delay interval (e.g., $LV_P$-$A_{P/S}$ in examples in which LV 32 is the later-depolarizing ventricle to which the fusion pacing stimulus is delivered) substantially corresponds to the ventricular filling time of heart 12 during a cardiac cycle. Thus, increasing the ventriculo-atrial delay interval may increase ventricular filling time of RV 28 and/or LV 32. In some examples, delivery of fusion pacing to LV 32 by IMD 16 may decrease the ventriculo-atrial delay interval. In some cases, the ventriculo-atrial delay interval may decrease to a time interval that does not permit sufficient ventricular filling. Insufficient ventricular filling may result in reduced cardiac output by heart 12, which may be undesirable. Techniques for modifying pacing therapy delivered by IMD 16 such that the ventriculo-atrial delay interval is maintained at or above a predetermined threshold value are described with respect to FIGS. 7-10. In some examples, the threshold is about 350 milliseconds (ms), although other thresholds are contemplated and may depend upon the particular patient 14 receiving the pacing therapy. Maintaining the ventriculo-atrial delay interval at or above a predetermined threshold value may help maintain a desirable level of cardiac output by heart 12 by dynamically controlling the ventricular filling time to be at or above a minimum duration.

Timing diagram 110 in FIG. 6 depicts an example in which RV 28 (FIG. 1) intrinsically depolarizes prior to LV 32 in the absence of ventricular pacing. In examples in which LV 32 intrinsically depolarizes prior to RV 28 in the absence of ventricular pacing, the timing diagram shown in FIG. 6 is modified such that the RV pacing event ($RV_P$) occurs at a time indicated by time marker 116 and the LV sensing event ($LV_S$) at a time indicated by time marker 118. In such a case, the calculation defined above by equation (3) may still be used to calculate the ventriculo-atrial delay for the second-to-depolarize ventricle, which in this case is the RV 28.

In additional examples, the ventriculo-atrial delay may be directly measured without using the calculation specified in equation (1). In such a case, IMD 16 directly measures the time duration between time marker 256 and time marker 254. The calculation in equation (1), however, may be advantageous because the ($A_{P/S}$-$A_{P/S}$) and ($A_{P/S}$-$V1_S$) measurements and the PEI parameter may already be available in existing fusion pacing systems. Since fusion pacing therapy systems may already provide these terms, the calculation in equation (1) may be able to be easily incorporated into measurement infrastructures that are already in-use by fusion pacing therapy systems. Thus, the ventriculo-atrial delay interval may be able to be obtained by adding additional post-processing to the raw data already obtained in existing fusion pacing therapy systems without the need to add additional hardware for the performance of physical raw data measurements. In addition, the measurements and calculation described in equation (1) may be able to utilize the same timing cycle used for suspension of ventricular pacing therapy as already used in fusion pacing therapy systems.

Figure 7:
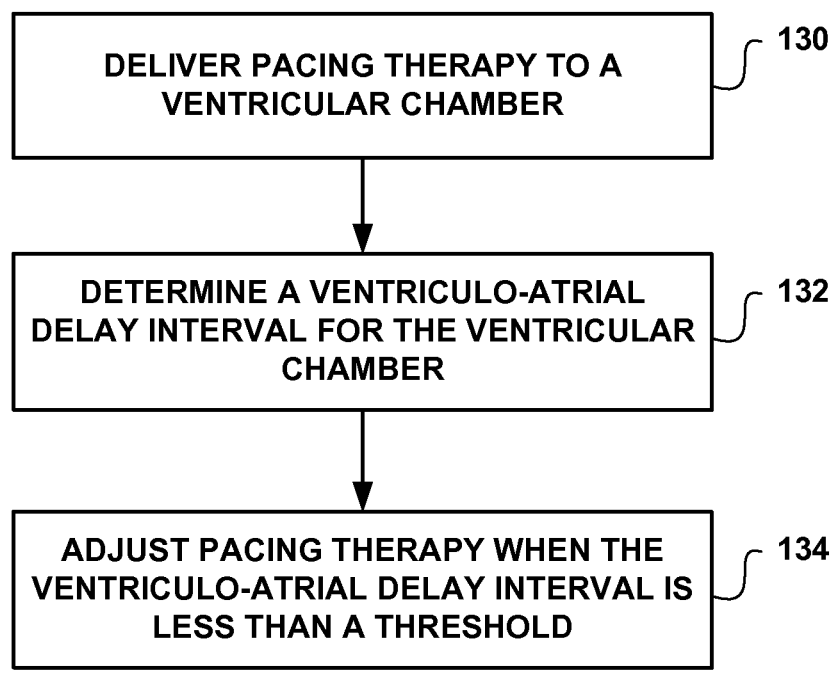
FIG. 7 is a flow diagram illustrating an example technique for adjusting pacing therapy based on ventriculo-atrial delay.

FIG. 7 is a flow diagram illustrating an example technique for adjusting pacing therapy based on a ventriculo-atrial delay, which may be determined, e.g., using equations 2 and 3 described above with respect to FIGS. 1 and 6, respectively. Processor 80 of IMD 16 (FIG. 4) may control signal generator 84 to deliver pacing therapy to a ventricular chamber of the heart (130). In some examples, the pacing therapy may be uni-ventricular pacing therapy, such as, for example, pre-excitation fusion pacing therapy. In some examples, the ventricular chamber is the later-depolarizing chamber in the absence of ventricular pacing. Thus, in some examples, the ventricular chamber is the LV 32, while in other examples, the ventricular chamber is the RV 28. The example technique shown in FIG. 7 is described with reference to the delivery of a pre-excitation fusion pacing pulse to LV 32. However, in other examples, the technique shown in FIG. 7 may also be applied to adjust therapy in examples in which RV 28 (FIG. 1) is the later-depolarizing ventricle and the excitation fusion pacing pulse is delivered to RV 28.

Processor 80 of IMD 16 determines a ventriculo-atrial delay interval for the ventricular chamber (132). In some examples, the ventriculo-atrial delay interval may be directly determined by detecting LV pace event ($LV_P$), detecting an atrial sensing or pace event ($A_{P/S}$) that is subsequent to the LV pace event, and determining a time interval between the LV pace event ($LV_P$) and the atrial sensing or pace event ($A_{P/S}$). In other examples, processor 80 indirectly determines the ventriculo-atrial delay interval based on other measurements or parameters as described above with respect to FIG. 6. In further examples, processor 80 may rely on other measurements performed by IMD 16 and/or an additional device external to IMD 16 in order to determine the ventriculo-atrial delay interval. For example, processor 80 may rely on pressure measurements, motion measurements, flow measurements, blood metabolite measurements, temperature measurements, and/or other mechanical or chemical measurement techniques that provide an indication of ventriculo-atrial delay and/or ventricular filling time.

Processor 80 controls signal generator 84 (FIG. 4) to adjust the pacing therapy when the ventriculo-atrial delay interval is less than a threshold (134). The ventriculo-atrial delay interval may be indicative of a ventricular filling time of the heart during a cardiac cycle. In one example, the threshold defines a minimum ventriculo-atrial delay interval value that is associated with a minimum desirable ventricular filling time. As previously indicated, a minimum desirable ventricular filling may be a filling time in which RV 28 or LV 32 fills to a level appropriate for providing patient 14 with the cardiac output necessary to meet the demands of the patient's body. In another example, the threshold defines a ventriculo-atrial delay interval value at which action should be taken to correct a decreasing ventricular filling time. Thus, when the ventriculo-atrial delay is below threshold, IMD 16 may adjust the pacing therapy in order to preserve and/or achieve acceptable ventricular filling times. In some examples, the threshold is about 350 milliseconds (ms), although other thresholds are contemplated and may depend upon the particular patient 14 receiving the pacing therapy.

In contrast to existing techniques, which use indirect measurements as surrogates for ventricular filling time, the techniques in this disclosure provide a metric for ventricular filling time that directly corresponds to a portion of the cardiac cycle when the ventricular filling actually takes place. The ventricular filling time metric may be, for example, the duration of the ventriculo-atrial interval. The use of a direct metric, as opposed to an indirect surrogate, may provide a more robust determination of ventricular filing time, which may be more sensitive to variations in the ventricular filling time that may not be detected by indirect measurements.

Figure 8:
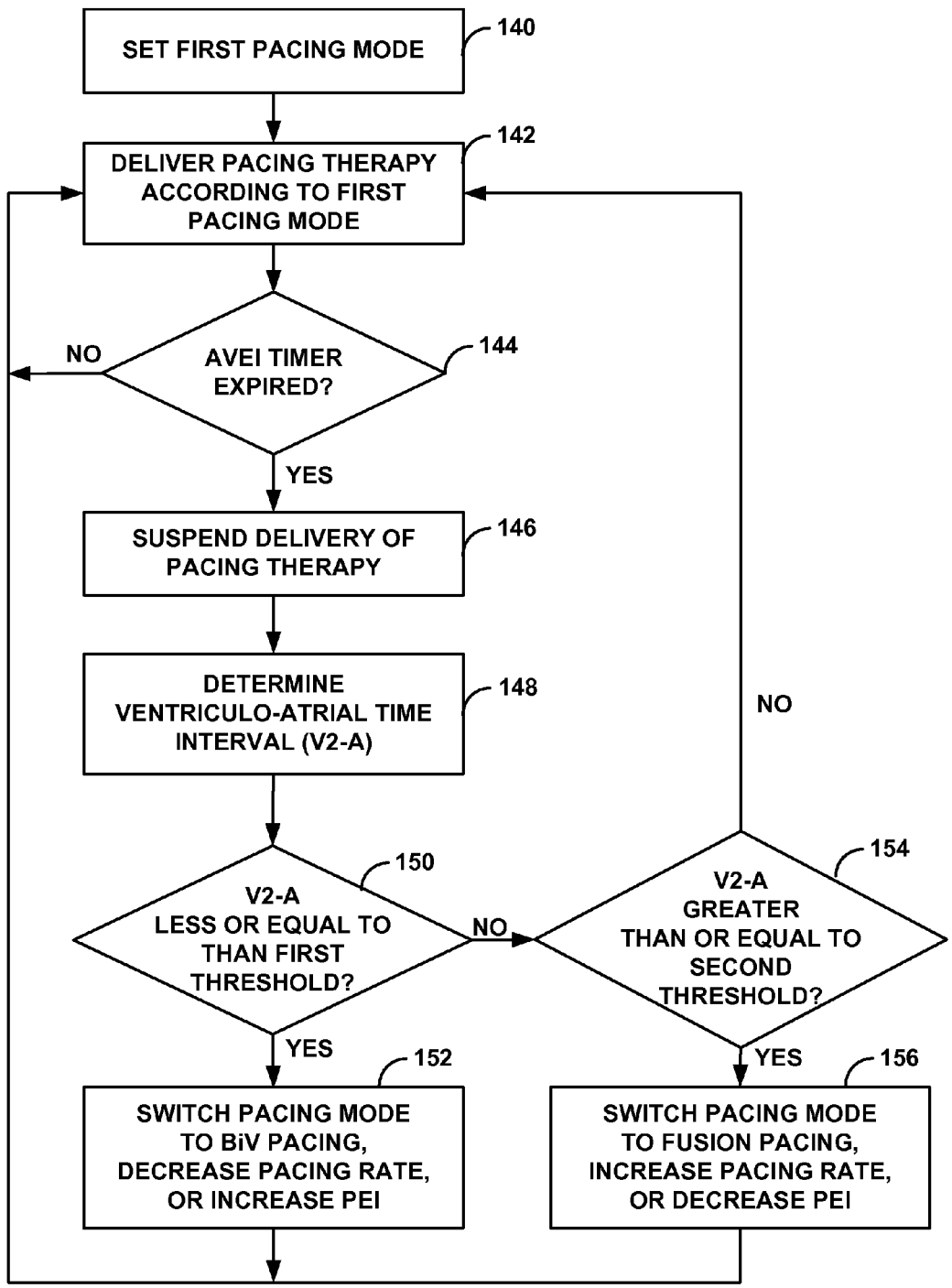
FIG. 8 is a flow diagram illustrating another example technique for adjusting pacing therapy based on ventriculo-atrial delay.

FIG. 8 is a flow diagram illustrating another example technique for adjusting pacing therapy based on a determined ventriculo-atrial delay. Processor 80 (FIG. 4) of IMD 16 may select a first pacing mode (140). The first pacing mode may be either a uni-ventricular pacing mode, such as a pre-excitation fusion pacing mode, or a biventricular pacing mode. In addition, IMD 16 may provide atrial pacing in either ventricular pacing mode. After setting the first pacing mode, processor 80 may control signal generator 84 (FIG. 4) to deliver pacing therapy according to the first pacing mode (142). During the delivery of therapy according to the first pacing mode, processor 80 may determine determines whether an atrio-ventricular evaluation interval (AVEI) timer has expired (144). The AVEI timer may be based on a programmable number of cardiac cycles (n-beats) and/or to a temporal value (n-seconds, n-minutes, etc.). In some examples, pacer timing and control module 92 (FIG. 4) of processor 80 may track the AVEI and generate an indication when the AVEI timer has expired.

In some examples, the AVEI timer may be programmed to a value within a range of about 1 second to about 16 hours. In other examples, the AVEI timer may be programmed to a value within a range of about 10 seconds to about 60 seconds. The programmable AVEI timer value may be increased or decreased by incremental steps in order to adjust the frequency of measurements that occur when the AVEI timer has expired. In general, a shorter AVEI timer value may be particularly useful in cases where the heart rate of patient 14 is rapidly changing, in cases where patient 14 is exercising, and/or in cases where more frequent measurements are desired. On the other hand, a longer AVEI timer value may be particularly useful in cases where the intrinsic AV nodal conduction does not occur within the heart (e.g., AV block), in cases in which patient 14 is resting, and/or in cases where less frequent measurements are desired.

If the AVEI timer has not expired, processor 80 may continue controlling signal generator 84 to deliver pacing therapy according to the first pacing mode (142). On the other hand, if the AVEI timer has expired, processor 80 suspends delivery of all or part of the pacing therapy (146). In other examples, IMD 16 does not suspend pacing therapy. After the pacing therapy according to the first pacing mode has been suspended, IMD 16 determines the ventriculo-atrial time interval (V2-A) for the second-to-depolarize ventricle (148). In some examples, the ventriculo-atrial delay interval may be directly measured. In other examples, the ventriculo-atrial delay may be derived and/or calculated from other measurements or parameters as described above with respect to FIGS. 6 and 7.

After determining the ventriculo-atrial time interval, IMD 16 determines if the ventriculo-atrial delay is less than or equal to a first threshold (150). The first threshold may be stored in memory 82 (FIG. 4) of IMD 16 or a memory of another device (e.g., programmer 24). In some examples, the first threshold defines a minimum value for an acceptable ventricular filling time. In other examples, the first threshold defines a ventriculo-atrial delay that indicates it is desirable to increase ventricular filling time.

If the ventriculo-atrial delay is less or equal to the first threshold, IMD 16 may determine that the ventriculo-atrial delay is shorter than desired, which may indicate that the pacing pulse to the later depolarizing ventricle (V2) is being delivered at a time that does not permit sufficient ventricular filling of heart 12. That is, if the ventriculo-atrial delay is less or equal to the first threshold, IMD 16 may determine that the ventricular filling time of heart 12 is below a desirable level. In order to increase the ventricular filling time of heart 12, processor 80 may adjust the pacing therapy in order to compensate for the low ventricular filling time (152).

Processor 80 adjusts the pacing therapy using any suitable technique that increases the ventriculo-atrial time interval. In examples in which the first pacing mode is a pre-excitation fusion pacing mode, processor 80 switch the pacing mode from a fusion pacing mode to a biventricular pacing mode. The biventricular pacing mode, in which IMD 16 delivers pacing stimuli to both RV 28 (FIG. 1) and LV 32 (FIG. 1) in order to resynchronize the depolarization of RV 28 and LV 32, may be associated with a shorter A-V delay than a pre-excitation fusion pacing mode. A shorter A-V delay for the first-to-depolarize ventricular chamber ($A_{P/S}$-$V1_S$) may be associated with a longer ventricular fill-time. For example, as shown in the timing diagram of FIG. 6, decreasing the $A_{P/S}$-$V1_S$ delay 124 may help increase the $V2_S$-$A_{P/S}$ interval 126, which may increase the ventricular fill time of heart 12, e.g., in cases where the $A_{P/S}$-$A_{P/S}$ interval is relatively constant. In some examples, IMD 16 may switch from a fusion pacing mode to a biventricular pacing mode having a fixed A-V delay, which may allow for a prolonged, and subsequently fixed, V-A interval to prolong filling times.

In other examples, processor 80 may adjust the pacing therapy (152) by decreasing the pacing rate and effectively increasing the duration of each cardiac cycle, which is indicated by ($A_{P/S}$-$A_{P/S}$). Increasing the duration of a cardiac cycle may increase ventricular fill time of heart 12 by increasing the $V2_S$-$A_{P/S}$ interval 126 (FIG. 6), which may correspond to the time in which RV 28 and LV 32 fill. In some cases, processor 80 may decrease the pacing rate such that the resultant cardiac rate is about 40 beats per minute.

In other examples, processor 80 may adjust the pacing therapy (152) by increasing the PEI, which processor 80 uses to time the delivery of the LV pacing pulse. As shown in FIG. 6, increasing the PEI, which corresponds to time interval 120, may increase the overall ventriculo-atrial time interval, which corresponds to time interval 126. Increasing the overall ventriculo-atrial time interval may increase the ventricular fill time of heart. In some examples, processor 80 may increase the PEI by increments of 10 ms or less. Processor 80 may select PEI to be in a range of about one ms to about 250 ms or more, such as about 100 ms to about 200 ms.

In some examples, processor 80 may execute a prioritized pacing adjustment scheme. For example, processor 80 may assign the switching of the pacing mode to a first highest priority, the adjustment of the pacing rate to a second highest priority, and the adjustment of the PEI to a third highest priority. In the event that the pacing needs to be adjusted, IMD 16 may start with the highest priority adjustment (i.e., switching the pacing mode). In some cases, however, the highest priority adjustment may not be available. For example, in a medical device where there is only a single lead, biventricular pacing may not be available. As a further example, the pacing mode may have already been switched and therefore a switch in pacing mode may no longer available. In any case, when the highest priority pacing adjustment is not available, IMD 16 may proceed to the second highest priority pacing adjustment.

In the example given above, the pacing adjustment having the second highest priority is an adjustment in the pacing rate. Similar to the modality switch described above, the pacing rate may not always be able to be adjusted. For example, the pacing rate may be set to a minimum value (e.g., for a particular patient activity level or for IMD 16 in general), and, therefore cannot be decreased any further. In such cases, IMD 16 may proceed to a third highest priority pacing adjustment, which is to adjust the PEI interval.

If processor 80 determines that the ventriculo-atrial delay is greater than or equal to the first threshold, IMD 16 determines whether the ventriculo-atrial delay is greater than a second threshold (154). The second threshold is greater than the first threshold, and may also be stored in memory 82 of IMD 16 or a memory of another device. In some examples, the second threshold defines a maximum value for an acceptable ventricular filling time. In other examples, the second threshold defines a ventriculo-atrial delay for which it is desirable to decrease ventricular filling time.

If the ventriculo-atrial delay is greater or equal to the second threshold, processor 80 may determine that the ventriculo-atrial delay is longer that desired. Accordingly, processor 80 adjusts the pacing therapy in order to decrease the ventriculo-atrial delay and decrease the ventricular filling time (156). Processor 80 may implement techniques similar to those discussed with respect to increasing the ventriculo-atrial delay in order to adjust the pacing therapy (156). However, rather than decreasing the pacing rate to decrease the heart rate, processor 80 may increase the pacing rate to increase the heart rate, and, in some cases, decrease the ventriculo-atrial delay. In addition, rather than increasing the PEI, processor 80 may decrease the PEI by increments of, e.g., 10 ms or less, in order to effectively decrease the ventriculo-atrial delay and decrease the ventricular fill time.

On the other hand, if the ventriculo-atrial delay is less than or equal to the second threshold, processor 80 may continue controlling signal generator 84 to deliver pacing therapy according to the first pacing mode (142) without necessarily performing any adjustments to the pacing therapy.

Although a three-tiered priority pacing adjustment scheme is described in this disclosure, any combination of pacing adjustments and prioritizations may be practiced with the techniques described in this disclosure. For example, IMD 16 may select between two different pacing adjustments when the ventriculo-atrial delay is less than or equal to a threshold. As another example, IMD 16 may simultaneously apply two different pacing adjustments in order to address a deviation from a desirable ventricular filling time. For example, IMD 16 may switch the pacing mode and adjust the pacing rate when the ventriculo-atrial delay interval is less than or equal to a threshold.

Figure 9:
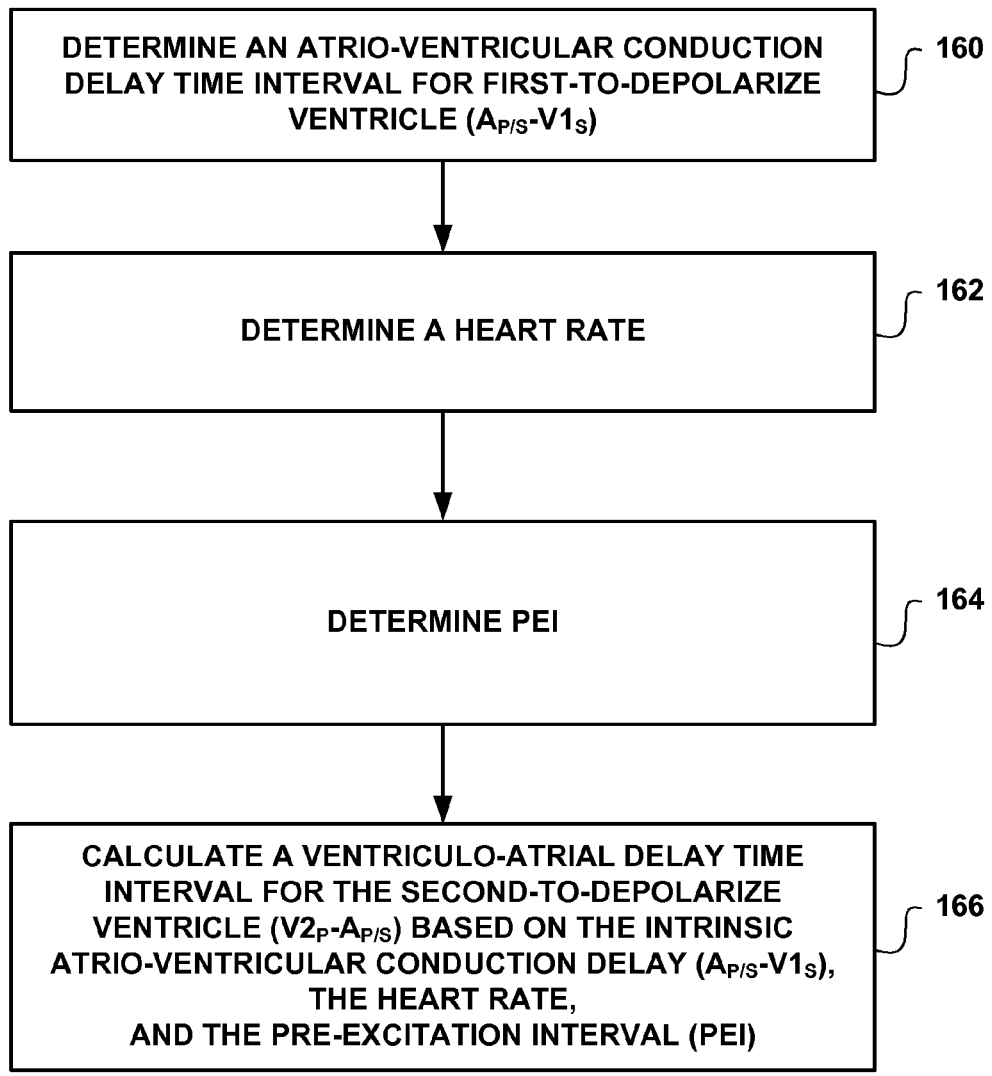
FIG. 9 is a flow diagram illustrating another example technique for determining ventriculo-atrial delay that may be used in the pacing adjustment schemes of FIGS. 6 & 7.

FIG. 9 is a flow diagram illustrating another example technique for determining ventriculo-atrial delay, which may be used in the pacing adjustment schemes of FIGS. 7 and 8. Processor 80 of IMD 16 determines an atrio-ventricular conduction delay time interval for a first-to-depolarize ventricle ($A_{P/S}$-$V1_S$) (160). In some examples, a mean or median of successive A-$V1_S$ measurements (e.g., 3 successive A-V1s measurements) may be used to determine the atrio-ventricular delay interval. In additional examples, the heart rate may be determined by taking a mean or average rate for a number of cardiac cycles (e.g. a 12 beat/cycle average).

Processor 80 also determines a heart rate of patient 14 at a time that substantially corresponds to the determination of the atrio-ventricular conduction delay time interval (162). The heart rate may be determined, for example, based on the time interval between successive atrial sensing or pace events, e.g., the $A_{P/S}$-$A_{P/S}$ interval. Processor 80 determines a PEI (164). In some examples, memory 82 of IMD 16 may store a current value for PEI. Processor 80 may determine the intrinsic atrio-ventricular conduction delay ($A_{P/S}$-$V1_S$) (160), the heart rate (162), and the pre-excitation interval (PEI) in any suitable order.

According to the technique shown in FIG. 9, processor 80 determines a ventriculo-atrial delay interval for the second-to-depolarize ventricle ($V2_P$-$A_{P/S}$) based on the intrinsic atrio-ventricular conduction delay ($A_{P/S}$-$V1_S$), the heart rate, and PEI (166). For example, processor 80 may determine the ventriculo-atrial delay interval using equations (2) or (3) provided above.

Figure 10:
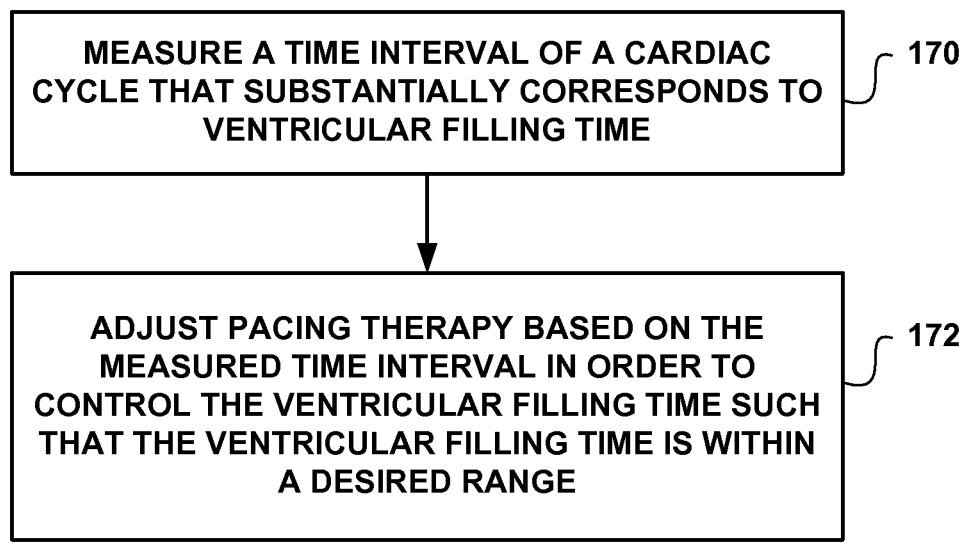
FIG. 10 is a flow diagram illustrating an example technique for adjusting the delivery of pacing therapy in order to preserve adequate ventricular filling times.

FIG. 10 is a flow diagram illustrating an example technique for adjusting pacing in order to preserve adequate ventricular filling times. IMD 16 measures a time interval of a cardiac cycle that substantially corresponds to a ventricular filling time (170). In some examples, IMD 16 may measure or determine the time interval that substantially corresponds to ventricular filling time based on electrical measures of cardiac activation. Such electrical measures of cardiac activation may include atrio-ventricular delay intervals, heart rates, pre-excitation intervals, and the like. In other examples, IMD 16 may measure or determine the time interval that substantially corresponds to ventricular filling time based on mechanical and/or chemical measurement techniques. Such techniques may include, for example, pressure measurements, motion measurements, flow measurements, blood metabolite measurements, and/or temperature measurements.

IMD 16 adjusts the pacing therapy based on the measured time interval in order to control the ventricular filling time such that the ventricular filling time is within a desired range (172). The desired range may correspond to ventricular filling times that are determined by a clinician to be acceptable for more than one patient or for a specific patient 14 during the delivery of uni-ventricular pacing therapy, such as pre-excitation fusion pacing therapy.

Figure 11:
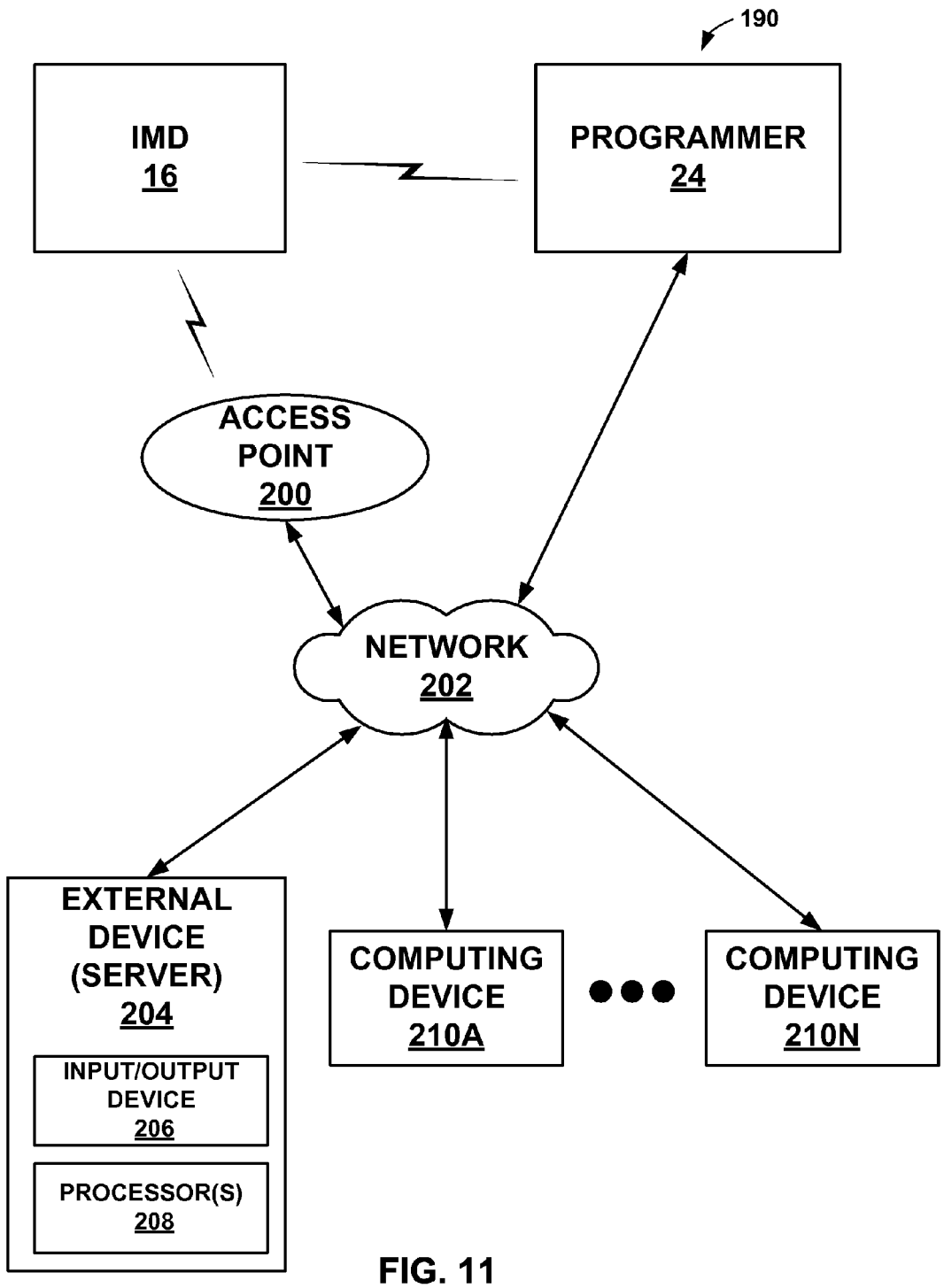
FIG. 11 is a block diagram illustrating an example system that includes an external device, such as a server, and one or more computing devices that are coupled to the IMD and programmer shown in FIG. 1 via a network.

FIG. 11 is a block diagram illustrating an example system 190 that includes an external device, such as a server 204, and one or more computing devices 210A-210N, that are coupled to the IMD 16 and programmer 24 shown in FIG. 1 via a network 202. In this example, IMD 16 may use its telemetry module 88 (FIG. 4) to communicate with programmer 24 via a first wireless connection, and to communication with an access point 200 via a second wireless connection. In the example of FIG. 11, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein. For example, as illustrated in FIG. 11, server 204 may comprise one or more processors 208 and an input/output device 206, which need not be co-located.

Server 204 may, for example, store EGM or ECG signals from IMD 16 or another sensing device, pacing intervals, one or more PEI values, ventriculo-atrial delay intervals, trends in ventriculo-atrial delay intervals, or trends in other cardiac cycle intervals over time. Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or one or more of the computing devices 210A-210N may perform any of the various functions or operations described herein.

Network 202 may comprise a local area network, wide area network, or global network, such as the Internet. System 190 may be implemented, in some aspects, with general network technology and functionality similar to that provided by the Medtronic CareLink® Network developed by Medtronic, Inc., of Minneapolis, Minn.

The techniques of this disclosure may be implemented by an IMD that is configured to provide uni-ventricular pacing, such as pre-excitation fusion pacing therapy, to a patient. The uni-ventricular pacing may be applied to either of the right or left ventricle of a heart. In some examples, the techniques of this disclosure may be implemented by an IMD that only delivers uni-ventricular pacing, and is not configured to deliver biventricular pacing. However, in some examples, the techniques of this disclosure may be implemented by an IMD that is configured to provide biventricular pacing therapy in addition to the uni-ventricular pacing. For example, the techniques of this disclosure may be implemented by an IMD that is capable of switching between uni-ventricular pacing mode and a biventricular pacing mode. The IMDs in any of these examples may also supply atrial pacing in addition to uni-ventricular and/or biventricular pacing.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   delivering pacing therapy to a ventricular chamber with an implantable medical device;
   determining a ventriculo-atrial delay interval for the ventricular chamber for at least one cardiac cycle;
   determining whether the ventriculo-atrial delay interval is less than or equal to a threshold; and
   adjusting the pacing therapy delivered by the implantable medical device when the ventriculo-atrial delay interval is less than or equal to the threshold; and
   wherein adjusting the pacing therapy comprises decreasing a pacing rate defined by the implantable medical device; and
   wherein determining the ventriculo-atrial delay interval comprises determining a time interval between an event of the ventricular chamber and a following atrial pacing event.

2. A method comprising:
   delivering pacing therapy to a ventricular chamber with an implantable medical device;
   determining a ventriculo-atrial delay interval for the ventricular chamber for at least one cardiac cycle;
   determining whether the ventriculo-atrial delay interval is less than or equal to a threshold; and
   adjusting the pacing therapy delivered by the implantable medical device when the ventriculo-atrial delay interval is less than or equal to the threshold; and
   wherein adjusting the pacing therapy comprises decreasing a pacing rate of the implantable medical device.

3. A method comprising:
   delivering pacing therapy to a ventricular chamber with an implantable medical device;
   determining a ventriculo-atrial delay interval for the ventricular chamber for at least one cardiac cycle;
   determining whether the ventriculo-atrial delay interval is less than or equal to a threshold; and
   adjusting the pacing therapy delivered by the implantable medical device when the ventriculo-atrial delay interval is less than or equal to the threshold; and
   wherein adjusting the pacing therapy comprises increasing a predetermined pre-excitation interval, wherein a pacing interval for delivering the pacing therapy to the ventricular chamber is based on the pre-excitation interval.

4. A method comprising:
   delivering pacing therapy to a ventricular chamber with an implantable medical device;
   determining a ventriculo-atrial delay interval for the ventricular chamber for at least one cardiac cycle;
   determining whether the ventriculo-atrial delay interval is less than or equal to a threshold; and
   adjusting the pacing therapy delivered by the implantable medical device when the ventriculo-atrial delay interval is less than or equal to the threshold; and
   wherein adjusting the pacing therapy comprises switching from a uni-ventricular pacing mode to a biventricular pacing mode.

5. The method of claim 2, wherein determining the ventriculo-atrial delay interval comprises determining a time interval between a pacing event of the ventricular chamber and an atrial sensing event or an atrial pacing event.

6. The method of claim 2, wherein determining the ventriculo-atrial delay interval comprises:
   determining a time interval between at least a first atrial sensing event or a first atrial pacing event and a second atrial sensing event or a second atrial pacing event; and
   decrementing the time interval by a pacing interval for delivering the pacing therapy to the ventricular chamber.

7. The method of claim 6, wherein the pacing interval comprises an atrio-ventricular delay interval for a second ventricular chamber incremented by a pre-excitation interval.

8. The method of claim 6, wherein determining the ventriculo-atrial delay interval comprises determining the ventriculo-atrial delay interval upon expiration of an atrio-ventricular evaluation interval timer.

9. The method of claim 2, wherein the threshold comprises a first threshold, the method further comprising further adjusting the pacing therapy delivered by the implantable medical device when the ventriculo-atrial delay interval is greater than or equal to a second threshold that is greater than the first threshold.

10. The method of claim 9, wherein further adjusting the pacing therapy delivered by the implantable medical device comprises at least one of decreasing a pre-excitation interval for pacing of the ventricular chamber or switching from a biventricular pacing mode to a fusion pacing mode.

11. The method of claim 1, wherein the threshold comprises a predetermined interval indicative of a minimum acceptable ventricular filling time interval for a human heart.

12. The method of claim 1, wherein delivering pacing therapy comprises delivering pre-excitation fusion pacing to the ventricular chamber.

13. The method of claim 12, wherein the ventricular chamber comprises a left ventricular chamber.

14. A system comprising:
a signal generator that generates and delivers pacing therapy to a ventricular chamber; and
a processor that determines a ventriculo-atrial delay interval for the ventricular chamber for at least one cardiac cycle, determines whether the ventriculo-atrial delay interval is less than or equal to a threshold, and adjusts the pacing therapy by the signal generator when the ventriculo-atrial delay interval is less than or equal to the threshold; and
wherein the processor adjusts the pacing therapy by at least controlling the signal generator to decrease a processor-defined pacing rate; and
wherein determining the ventriculo-atrial delay interval comprises determining a time interval between an event of the ventricular chamber and a following atrial pacing event.

15. A system comprising:
a signal generator that generates and delivers pacing therapy to a ventricular chamber; and
a processor that determines a ventriculo-atrial delay interval for the ventricular chamber for at least one cardiac cycle, determines whether the ventriculo-atrial delay interval is less than or equal to a threshold, and adjusts the pacing therapy by the signal generator when the ventriculo-atrial delay interval is less than or equal to the threshold; and
wherein the processor adjusts the pacing therapy by at least controlling the signal generator to decrease a pacing rate.

16. A system comprising:
a signal generator that generates and delivers pacing therapy to a ventricular chamber; and
a processor that determines a ventriculo-atrial delay interval for the ventricular chamber for at least one cardiac cycle, determines whether the ventriculo-atrial delay interval is less than or equal to a threshold, and adjusts the pacing therapy by the signal generator when the ventriculo-atrial delay interval is less than or equal to the threshold; and
wherein the processor adjusts the pacing therapy by at least increasing a predetermined pre-excitation interval, wherein a pacing interval with which the signal generator delivers the pacing therapy to the ventricular chamber is based on the pre-excitation interval.

17. A system comprising:
a signal generator that generates and delivers pacing therapy to a ventricular chamber; and
a processor that determines a ventriculo-atrial delay interval for the ventricular chamber for at least one cardiac cycle, determines whether the ventriculo-atrial delay interval is less than or equal to a threshold, and adjusts the pacing therapy by the signal generator when the ventriculo-atrial delay interval is less than or equal to the threshold; and
wherein the processor adjusts the pacing therapy by at least controlling the signal generator to switch from a univentricular pacing mode to a biventricular pacing mode.

18. The system of claim 15, wherein the processor determines the ventriculo-atrial delay interval by at least determining a time interval between a pacing event of the ventricular chamber and an atrial sensing event or an atrial pacing event.

19. The system of claim 15, wherein the processor determines the ventriculo-atrial delay interval by at least determining a time interval between at least a first atrial sensing event or a first atrial pacing event and a second atrial sensing event or a second atrial pacing event, and decrementing the time interval by a pacing interval for delivering the pacing therapy to the ventricular chamber.

20. The system of claim 19, wherein the pacing interval comprises an atrio-ventricular delay interval for a second ventricular chamber incremented by a pre-excitation interval.

21. The system of claim 14, wherein the processor determines the ventriculo-atrial delay interval upon expiration of an atrio-ventricular evaluation interval timer.

22. The system of claim 14, wherein the threshold comprises a first threshold, and the processor further adjusts the pacing therapy delivered by the implantable medical device when the ventriculo-atrial delay interval is greater than or equal to a second threshold that is greater than the first threshold.

23. The system of claim 22, wherein the processor further adjusts the pacing therapy delivered by the implantable medical device by at least one of decreasing a pre-excitation interval for the pacing therapy or controlling the signal generator to switch from a biventricular pacing mode to a fusion pacing mode.

24. The system of claim 14, wherein the threshold comprises a predetermined interval indicative of a minimum acceptable ventricular filling time interval for a human heart.

25. The system of claim 14, wherein the pacing therapy comprises pre-excitation fusion pacing therapy.

26. A system comprising:
means for delivering pacing therapy to a ventricular chamber with an implantable medical device;
means for determining a ventriculo-atrial delay interval for the ventricular chamber for at least one cardiac cycle;
means for determining whether the ventriculo-atrial delay interval is less than or equal to a threshold; and
means for adjusting the pacing therapy delivered by the implantable medical device when the ventriculo-atrial delay interval is less than or equal to the threshold; and
wherein the means for adjusting the pacing therapy comprises means for decreasing a defined pacing rate of the implantable medical device; and
wherein the means for determining the ventriculo-atrial delay interval comprises means for determining a time interval between an event of the ventricular chamber and a following atrial pacing event.

27. A system comprising:
means for delivering pacing therapy to a ventricular chamber with an implantable medical device;

means for determining a ventriculo-atrial delay interval for the ventricular chamber for at least one cardiac cycle;

means for determining whether the ventriculo-atrial delay interval is less than or equal to a threshold; and means for adjusting the pacing therapy delivered by the implantable medical device when the ventriculo-atrial delay interval is less than or equal to the threshold; and wherein the means for adjusting the pacing therapy comprises means for switching from a uni-ventricular pacing mode to a biventricular pacing mode.

28. A system comprising:

means for delivering pacing therapy to a ventricular chamber with an implantable medical device;

means for determining a ventriculo-atrial delay interval for the ventricular chamber for at least one cardiac cycle;

means for determining whether the ventriculo-atrial delay interval is less than or equal to a threshold; and means for adjusting the pacing therapy delivered by the implantable medical device when the ventriculo-atrial delay interval is less than or equal to the threshold; and wherein the means for adjusting the pacing therapy comprises means for increasing a predetermined pre-excitation interval, wherein a pacing interval for delivering the pacing therapy to the ventricular chamber is based on the pre-excitation interval.

29. A system comprising:

means for delivering pacing therapy to a ventricular chamber with an implantable medical device;

means for determining a ventriculo-atrial delay interval for the ventricular chamber for at least one cardiac cycle;

means for determining whether the ventriculo-atrial delay interval is less than or equal to a threshold; and means for adjusting the pacing therapy delivered by the implantable medical device when the ventriculo-atrial delay interval is less than or equal to the threshold; and wherein the means for adjusting the pacing therapy comprises means for decreasing a pacing rate of the implantable medical device.

30. The system of claim 29, wherein the means for determining the ventriculo-atrial delay interval comprises means for determining a time interval between a pacing event of the ventricular chamber and an atrial sensing event or an atrial pacing event.

* * * * *